US010595818B2

(12) United States Patent
Levine

(10) Patent No.: US 10,595,818 B2
(45) Date of Patent: Mar. 24, 2020

(54) MEDICAL SYSTEMS AND METHODS FOR DENSITY ASSESSMENT USING ULTRASOUND

(71) Applicant: Makaha Medical, LLC., Pottstown, PA (US)

(72) Inventor: Marc-Alan Levine, Pottstown, PA (US)

(73) Assignee: Makaha Medical, LLC., Pottstown, PA (US)

( * ) Notice: Subject to any disclaimer, the term of this patent is extended or adjusted under 35 U.S.C. 154(b) by 312 days.

(21) Appl. No.: 15/436,820

(22) Filed: Feb. 19, 2017

(65) Prior Publication Data
US 2017/0265839 A1 Sep. 21, 2017

Related U.S. Application Data

(60) Provisional application No. 62/310,679, filed on Mar. 19, 2016.

(51) Int. Cl.
A61B 8/08 (2006.01)
A61B 5/11 (2006.01)
(Continued)

(52) U.S. Cl.
CPC .......... *A61B 8/085* (2013.01); *A61B 5/02007* (2013.01); *A61B 5/1126* (2013.01); *A61B 5/1459* (2013.01); *A61B 5/14539* (2013.01); *A61B 5/14542* (2013.01); *A61B 5/4848* (2013.01); *A61B 5/6851* (2013.01); *A61B 5/6852* (2013.01); *A61B 8/12* (2013.01); *A61B 8/445* (2013.01); *A61B 8/5223* (2013.01); *A61B 17/2202* (2013.01); *A61B 8/0833* (2013.01); *A61B 8/0891* (2013.01);
(Continued)

(58) Field of Classification Search
CPC .......... A61B 8/12; A61B 8/445; A61B 8/085; A61B 8/0833; A61B 2018/00994; A61B 17/2202; A61B 17/22; A61B 5/6852; A61B 5/02007; A61M 25/10
See application file for complete search history.

(56) References Cited

U.S. PATENT DOCUMENTS

| 4,319,580 | A | 3/1982 | Colley et al. |
| 4,354,502 | A | 10/1982 | Colley et al. |

(Continued)

FOREIGN PATENT DOCUMENTS

| WO | WO 2010/030882 | 3/2010 |
| WO | WO 2010/075565 | 7/2010 |
| WO | WO 2013/181137 | 12/2013 |

OTHER PUBLICATIONS

European Search Report 17162096.6-1657 dated Aug. 2017.
(Continued)

*Primary Examiner* — Angela M Hoffa
*Assistant Examiner* — Virag B Patel
(74) *Attorney, Agent, or Firm* — Neil D. Gershon

(57) ABSTRACT

A medical system and method for density assessment utilizing ultrasound. The system includes a guidewire configured and dimensioned for insertion in the vessel of the patient, a sensor positioned at the distal portion of the elongated member and a connector connecting the elongated member to an indicator, the sensor determining the density and the indicator providing an indication of the determined density.

19 Claims, 29 Drawing Sheets

(51) Int. Cl.
*A61B 5/145* (2006.01)
*A61B 5/00* (2006.01)
*A61B 8/12* (2006.01)
*A61B 17/22* (2006.01)
*A61B 8/00* (2006.01)
*A61B 5/02* (2006.01)
*A61B 5/1459* (2006.01)
*A61B 17/00* (2006.01)

(52) U.S. Cl.
CPC .............. *A61B 8/4494* (2013.01); *A61B 8/461* (2013.01); *A61B 8/467* (2013.01); *A61B 2017/00022* (2013.01); *A61B 2017/00035* (2013.01); *A61B 2017/00106* (2013.01)

(56) References Cited

U.S. PATENT DOCUMENTS

| | | | |
|---|---|---|---|
| 5,054,882 | A | 10/1991 | Riccitelli et al. |
| 5,125,410 | A | 6/1992 | Misono et al. |
| 5,271,398 | A | 12/1993 | Schlain et al. |
| 5,307,816 | A | 5/1994 | Hashimoto et al. |
| 5,348,015 | A | 9/1994 | Moehring et al. |
| 5,441,051 | A | 9/1995 | Hileman et al. |
| 5,477,860 | A | 12/1995 | Essen-Moller |
| 5,522,389 | A | 6/1996 | Fischer et al. |
| 5,743,259 | A | 4/1998 | Kruse et al. |
| 5,848,965 | A | 12/1998 | Essen-Moller |
| 5,928,155 | A | 7/1999 | Eggers et al. |
| 6,125,290 | A | 9/2000 | Miesel |
| 6,125,291 | A | 9/2000 | Miesel et al. |
| 6,134,459 | A | 10/2000 | Roberts et al. |
| 6,198,952 | B1 | 3/2001 | Miesel |
| 6,258,046 | B1 | 7/2001 | Kimball et al. |
| 6,731,976 | B2 | 5/2004 | Penn et al. |
| 6,939,313 | B2 | 9/2005 | Saadat et al. |
| 7,181,261 | B2 | 2/2007 | Silver et al. |
| 7,603,166 | B2 | 10/2009 | Casscells, III et al. |
| 7,618,376 | B2 | 11/2009 | Kimball |
| 7,747,301 | B2 | 6/2010 | Cheng et al. |
| 7,801,626 | B2 | 9/2010 | Moser |
| 8,000,784 | B2 | 8/2011 | Ferren et al. |
| 8,103,361 | B2 | 1/2012 | Moser |
| 8,226,578 | B2 | 7/2012 | Von Malmborg |
| 8,231,537 | B2 | 7/2012 | Ahmed et al. |
| 8,275,438 | B2 | 9/2012 | Simpson et al. |
| 8,298,142 | B2 | 10/2012 | Simpson et al. |
| 8,364,230 | B2 | 1/2013 | Simpson et al. |
| 8,425,416 | B2 | 4/2013 | Brister et al. |
| 8,449,464 | B2 | 5/2013 | Simpson et al. |
| 8,454,521 | B2 | 6/2013 | Mochizuki |
| 8,454,524 | B2 | 6/2013 | Kassem |
| 8,532,730 | B2 | 9/2013 | Brister et al. |
| 8,637,320 | B2 | 1/2014 | Schubert et al. |
| 8,639,309 | B2 | 1/2014 | Schuler |
| 8,744,544 | B2 | 6/2014 | Najafi et al. |
| 8,828,320 | B2 | 9/2014 | Bardell et al. |
| 8,862,197 | B2 | 10/2014 | Kamath et al. |
| 9,089,287 | B2 * | 7/2015 | Sliwa, Jr. ............. A61B 8/0841 |
| 2002/0068928 | A1 | 6/2002 | Werneth |
| 2004/0133079 | A1 | 7/2004 | Mazar et al. |
| 2005/0215946 | A1 * | 9/2005 | Hansmann ............. A61B 5/027 |
| | | | 604/66 |
| 2006/0079923 | A1 | 4/2006 | Chhabra et al. |
| 2006/0100639 | A1 * | 5/2006 | Levin ............. A61M 25/10182 |
| | | | 606/106 |
| 2006/0253023 | A1 | 11/2006 | Lewis et al. |
| 2007/0066929 | A1 | 3/2007 | Ferren et al. |
| 2008/0249409 | A1 * | 10/2008 | Fraser .................. A61B 8/0833 |
| | | | 600/439 |
| 2009/0043191 | A1 | 2/2009 | Castella et al. |
| 2009/0105799 | A1 | 4/2009 | Hekmat et al. |
| 2009/0203064 | A1 | 8/2009 | Ericson |
| 2009/0264771 | A1 * | 10/2009 | Houben ............. A61B 5/02007 |
| | | | 600/470 |
| 2009/0318757 | A1 | 12/2009 | Singh |
| 2010/0036209 | A1 | 2/2010 | Ferren et al. |
| 2011/0077528 | A1 | 3/2011 | Kemp et al. |
| 2012/0004547 | A1 * | 1/2012 | Harks .................. A61B 8/0858 |
| | | | 600/439 |
| 2012/0108968 | A1 | 5/2012 | Freiburger et al. |
| 2013/0211292 | A1 | 8/2013 | Sverdlik et al. |
| 2014/0114144 | A1 * | 4/2014 | Levine ................. A61B 5/6852 |
| | | | 600/301 |
| 2014/0180069 | A1 | 6/2014 | Millett |
| 2014/0194704 | A1 | 7/2014 | Millett et al. |
| 2014/0200438 | A1 | 7/2014 | Millett et al. |
| 2014/0276024 | A1 * | 9/2014 | Stigall ..................... A61M 5/00 |
| | | | 600/427 |
| 2015/0088190 | A1 | 3/2015 | Jensen |
| 2016/0206373 | A1 * | 7/2016 | Chen .................. A61B 18/1492 |
| 2016/0287278 | A1 * | 10/2016 | Stigall .................. A61B 5/0084 |
| 2016/0374703 | A1 * | 12/2016 | Yu ...................... A61B 17/2202 |
| | | | 606/128 |

OTHER PUBLICATIONS

Cell Death and Differentiation (2004), "Alterations of intracellular pH homeostasis in apoptosis: origins and roles", D. Lagadic-Gossmann, L. Huc and V. Lecureur, p. 953-961.

Seminars in Nuclear Medicine, vol. XXXIII, No. 1 (Jan. 2003), "Neuroimaging in Cerebrovascular Disorders: Measurement of Cerebral Physiology After Stroke and Assessment of Stroke Recovery", J.M. Mountz, H.G. Liu and G. Deutsch, p. 56-76.

Laboratory Animals Ltd. Laboratory Animals (2003) 37, "$CO_2$ induced acute respiratory acidosis and brain tissue intracellular pH: a $^{31}$P NMR study in swine", L. Martoft, H. Stodkilde-Jorgensen, A. Forslid, H.D. Pedersen and P.F. Jorgensen, p. 241-248.

Makaha Medical, Proof of Concept Experiment, Revision: A, Document No. MMTR 122612-01, M. Levine, Date of Experiment: Dec. 14, 2012.

Normal Breathing Defeats Chronic Diseases, "$CO_2$, Blood pH and Respiratory Alkalosis", www.NormalBreathing.com.

Interface Focus published online Mar. 23, 2011, "Modelling of pH dynamics in brain cells after stroke", P. Orlowski, M. Chappell, C.S. Park, V. Grau and S. Payne, p. 1-9.

Khatri, Rakesh, et al. "Blood-brain barrier, reperfusion injury, and hemorrhagic transformation in acute ischemic stroke." Neurology 79.13 Supplement 1 (2012): S52-S57.

"Acidosis and Alkolosis." Anatomy & Physiology 5/e Student Online Learning Center. The McGraw-Hill Companies, 1998. Web. Dec. 9, 2016.

Kummer V. "Cerebral Hemorrhage Following Thrombolysis in Stroke" Stroke Update 2002.

* cited by examiner

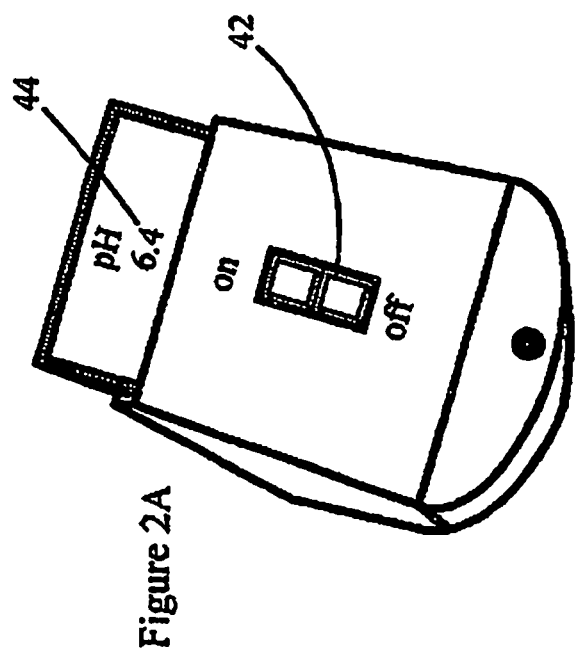

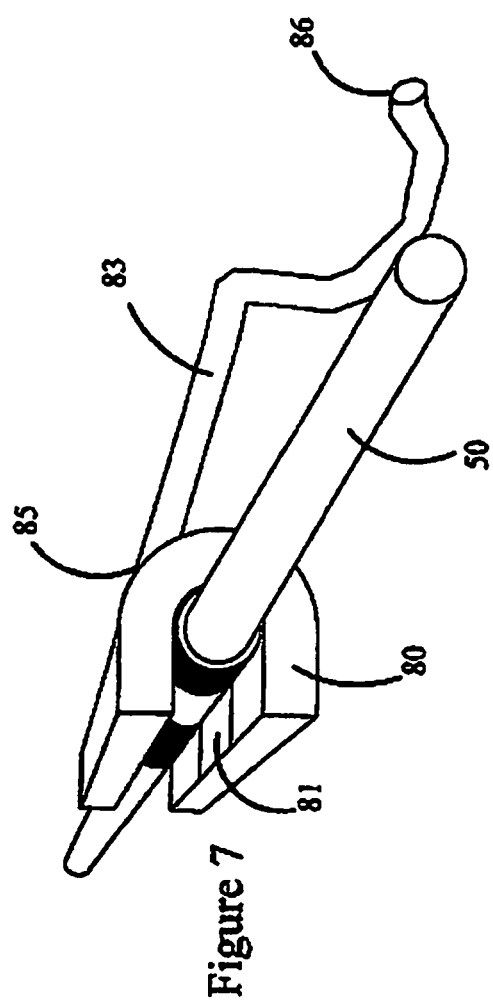

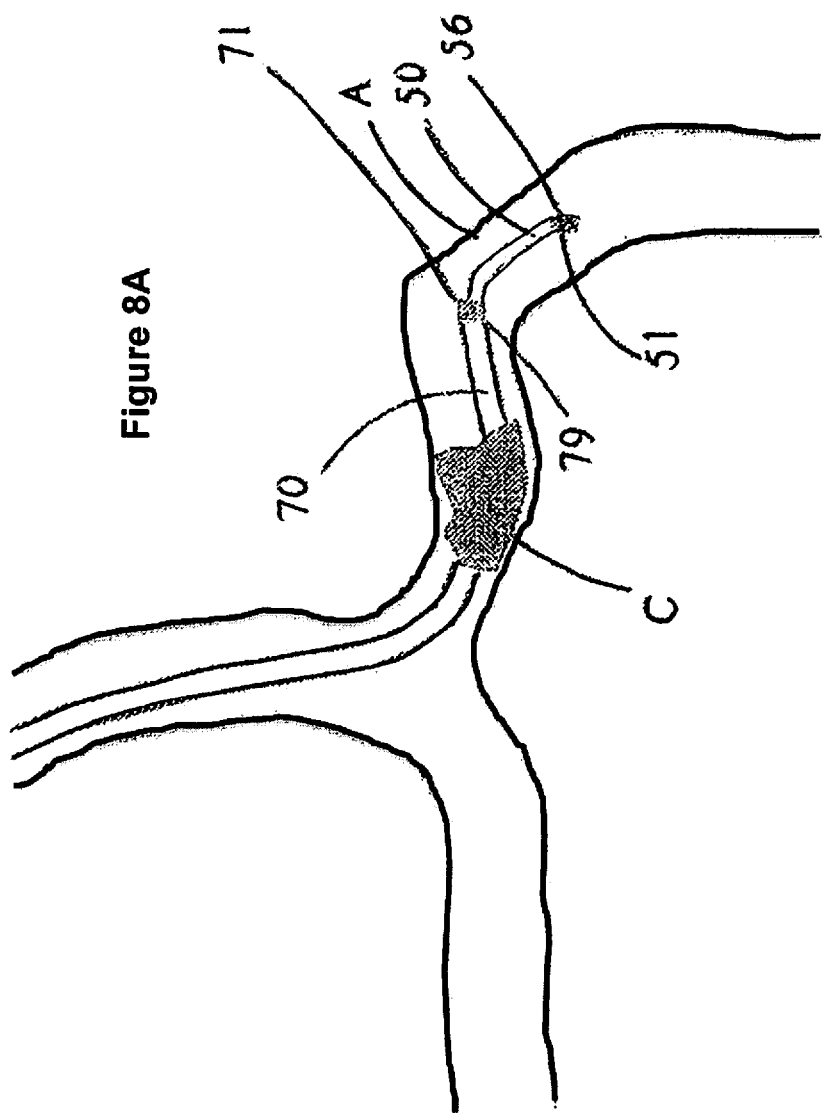

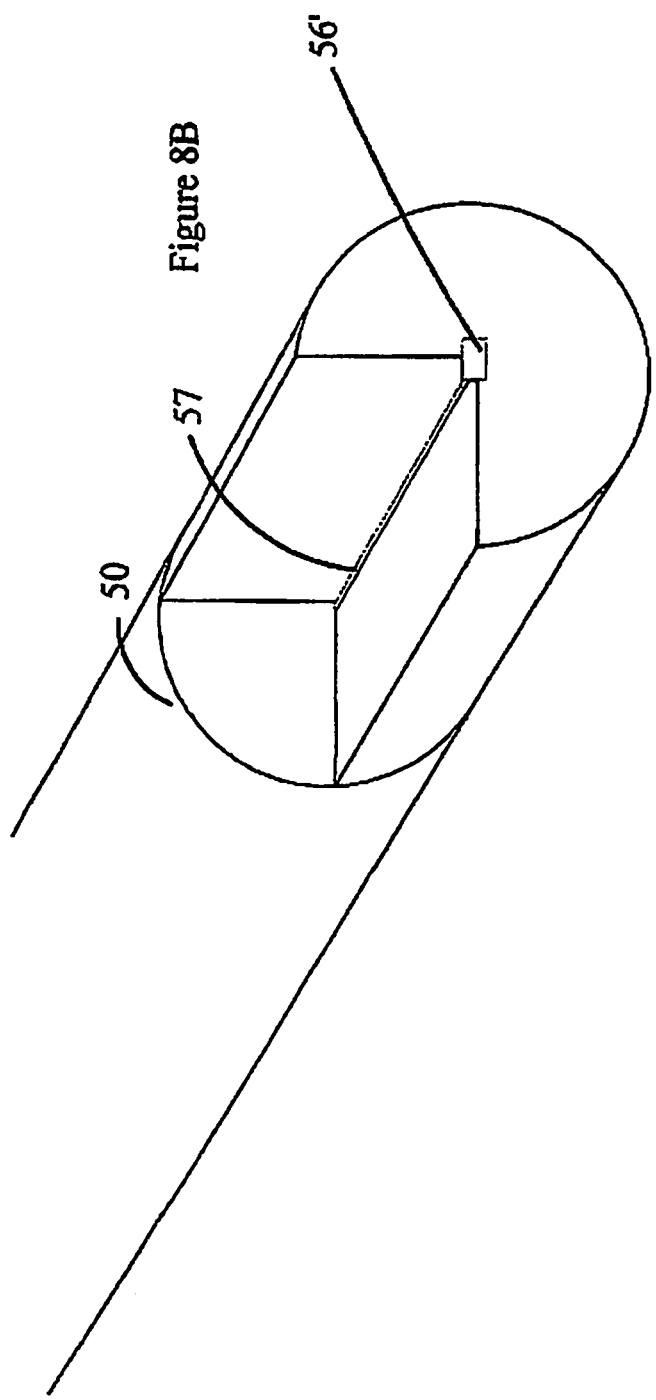

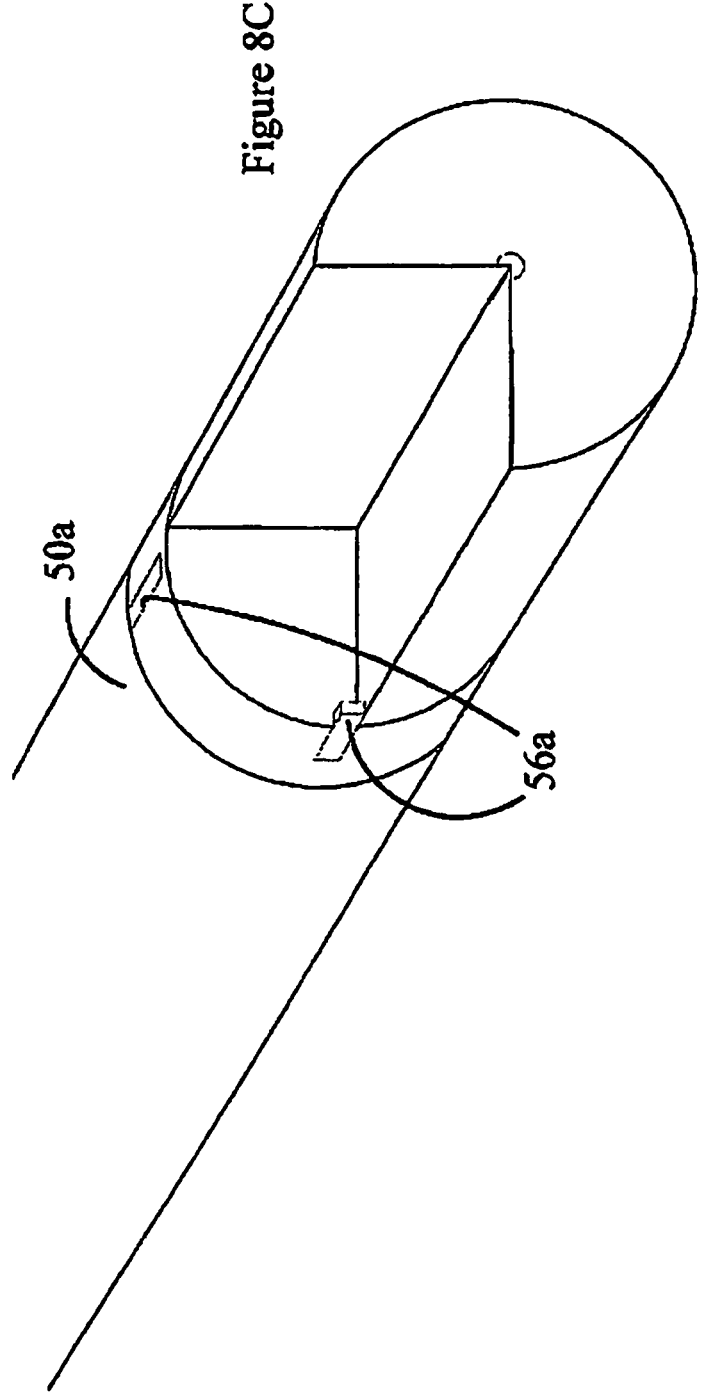

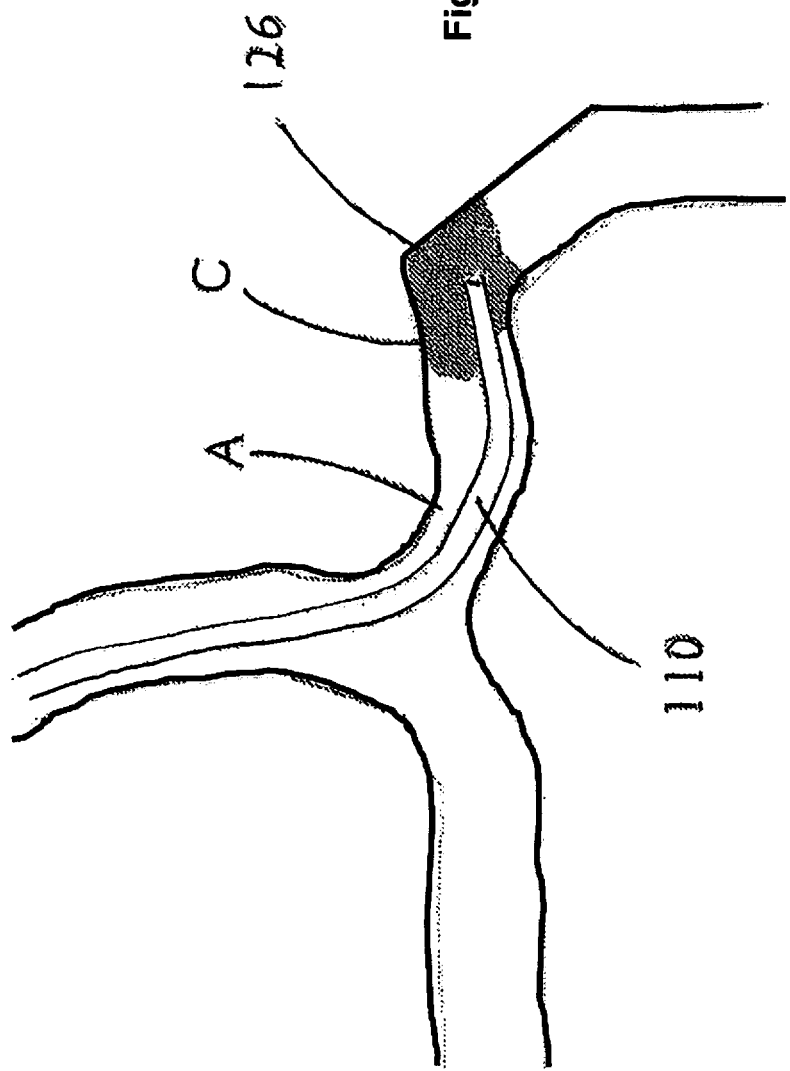

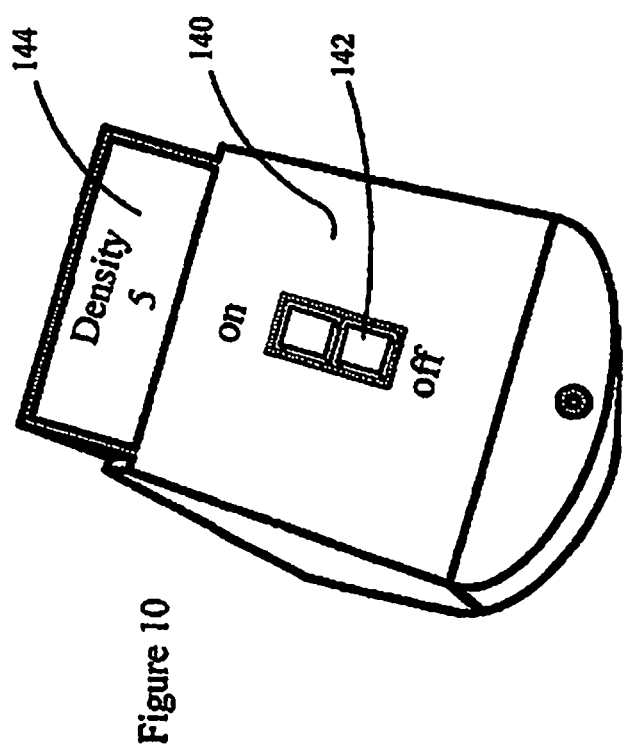

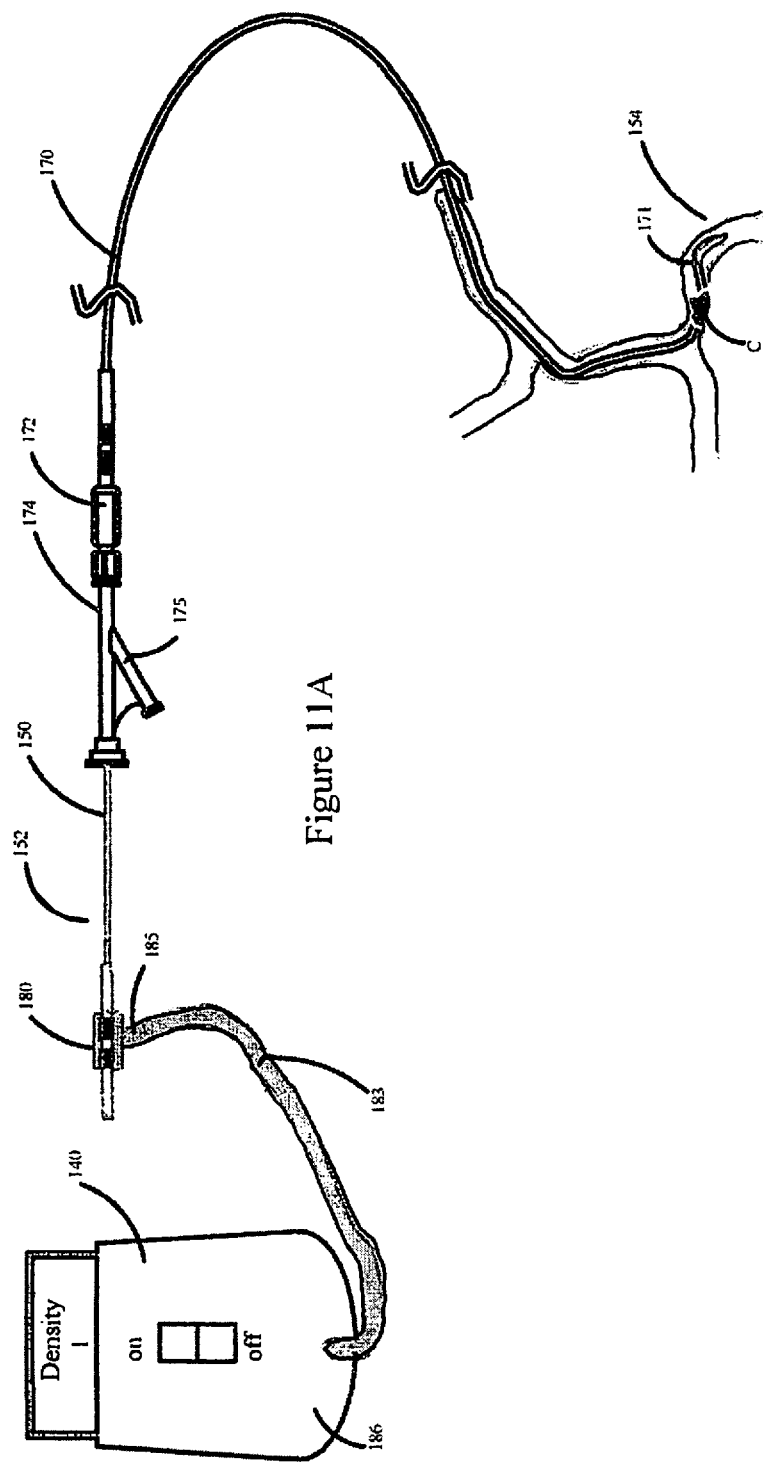

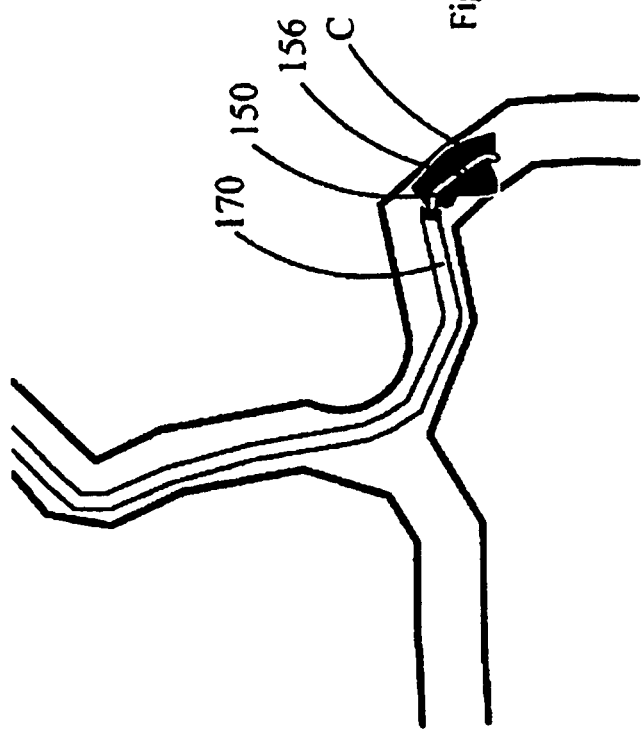

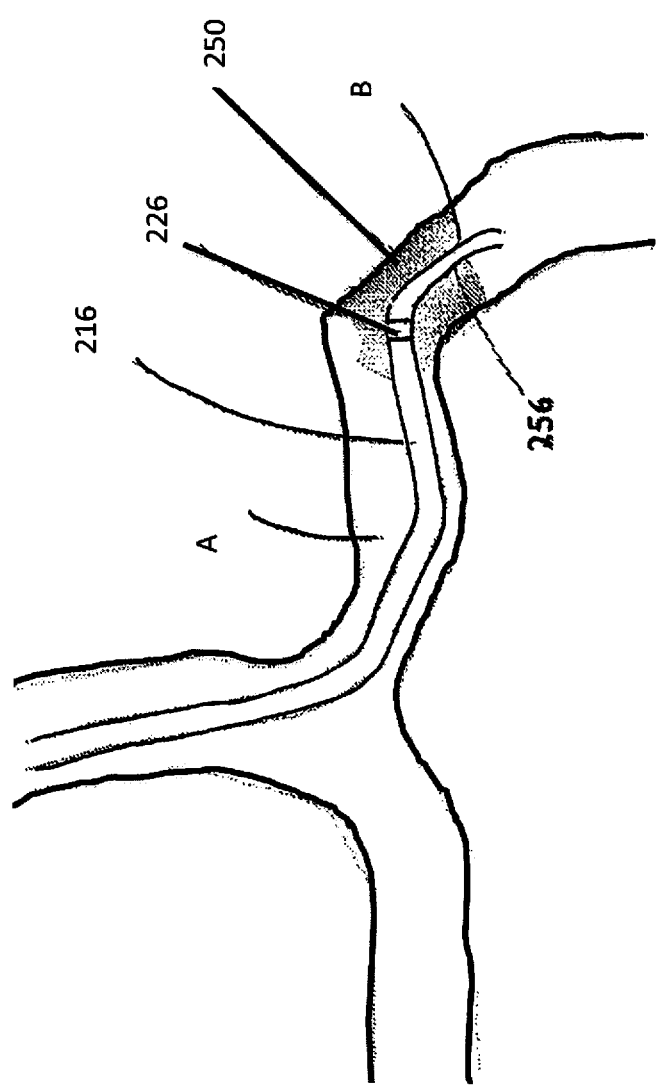

MEDICAL SYSTEMS AND METHODS FOR DENSITY ASSESSMENT USING ULTRASOUND

This application claims priority from provisional application Ser. No. 62/310,649, filed Mar. 19, 2016, the entire contents of which are incorporated herein by reference.

BACKGROUND

Technical Field

This application relates to an ultrasound system and method for determining density.

Background of Related Art

Cerebrovascular disease refers to diseases of the brain caused by vascular abnormalities which result in abnormal cerebral blood flow. The most common cause of cerebrovascular disease is narrowing of the major arteries supplying blood to the brain, resulting in thrombogenic disease or sudden occlusion of blood flow, which if large enough results in ischemic stroke.

Clots (Ischemic Stroke) can originate in various areas and be caused by different modalities. These different modalities create clots that vary in consistency. The clot can be platelet rich (runny) or fibrin rich (hard) or anywhere in between the two. Ischemic stroke is caused by the thrombosis of a major vessel supplying blood to a region of the brain. A shortage of blood in the cerebral tissue leads to the deletion of metabolites such as oxygen and glucose, which in turn causes depletion of energy stores of the cells. Therefore, it is critical to remove the clots to restore adequate blood supply to the brain.

Current treatments for clot removal include application of thrombolytic drugs to dissolve the clot, aspiration, and mechanical thrombectomy devices in minimally invasive procedures. A problem encountered with these approaches is that the composition of the clot is undetectable in situ, while the efficacy of these approaches is dependent in part on the clot composition. Therefore, the physician is taking one of the known approaches for treatment of the clot without the knowledge of the clot makeup, e.g., its consistency. This can lead to inconsistent results as well as failure to properly treat the clot.

It would therefore be beneficial if the surgeon could identify the type of clot beforehand to better assess how the clot could be treated. Such prior knowledge would greatly enhance clot removal as the surgeon can adapt the approach to better match the treatment device or drugs with the type of clot.

Although techniques for identifying characteristics of blood clots are known, the need exists for a simple, reliable, easy to use and low profile system for clot assessment. It would also be beneficial to provide such system which can effectively assess blood clot characteristics at various times during the procedure.

Moreover, in addition to determining the type of blood clot, it would also be beneficial to assess whether the blood clot has been effectively removed during the procedure without relying on current methods, such as injecting contrast, which can have adverse effects such as re-compacting the clot.

In addition, in cerebrovascular disease, the vitality of the vasculature distal to the clot is compromised once the clot lodges in place. Vasculature that has been deprived of oxygenated blood will necrose and become friable. Once blood flow is restored after clot removal, such blood flow could potentially cause a hemorrhagic event, which means the vessel can bleed out and burst open. Currently, surgeons do not have adequate knowledge of the vasculature downstream of the clot and therefore cannot accurately assess the risk of clot removal by for example dissolution, aspiration or mechanical thrombectomy.

It would be beneficial if the surgeon could determine the health of the vasculature distal to the clot prior to removal of the clot so the surgeon could determine if clot removal is advisable and/or take necessary precautions during clot removal so the vessels are not compromised. Prior attempts to measure pH using magnetic resonance imaging (MRI) technique have been attempted, as explained for example in "Modelling of pH Dynamics in Brain Cells After Stroke", by Piotr Orlowski, et al., published in Interface Focus, The Royal Society, 2011. However, these attempts to date have been unsuccessful. Additionally, relying on MRI is very expensive and requires relatively complex mathematical models. Further, an ischemic event might need to be treated in an ambulance prior to arrival at a hospital and thus an MRI is not possible. Therefore, although the role of pH of the vasculature is recognized, the need exists to utilize this parameter to readily and inexpensively determine in hospital and non-hospital settings vascular tissue health to enhance blood clot removal or prevent clot removal where the risk is too great. This would provide great benefits not only for hospital treatment but for pre-hospital treatment such as in the ambulance or home prior to arrival at the hospital.

Additionally, after assessment of the health of the vasculature and selection of the proper clot treatment, it might be beneficial to control the restoration of blood flow. Being able to determine the health of the vasculature would thus advantageously enable gradual return of blood flow if deemed necessary to reduce the risk of hemorrhaging.

SUMMARY OF THE INVENTION

The present invention provides in one aspect an ultrasound system for determining a density of a blood clot in a vessel of a patient prior to and during removal of the blood clot. The system includes a flexible elongated member configured and dimensioned for insertion in the vessel of the patient and having a distal portion configured for insertion adjacent the blood clot, the elongated member configured to position a catheter thereover. A sensor is positioned at the distal portion of the elongated member and a connector connects the elongated member to an indicator, the sensor determining the density of the blood clot utilizing ultrasound sending signals from within the vessel and the indicator providing an indication of the determined density of the blood clot to determine a treatment method for the blood clot and to track removal of the blood clot.

In some embodiments, the elongated member is a guidewire. In some embodiments, the guidewire includes a marker band and the sensor is positioned within the marker band.

In some embodiments, the sensor includes a transmitter for transmitting ultrasonic waves toward the blood clot, and the density of the blood clot is determined by ultrasonic wave feedback as the density decreases as portions of the clot are removed. In some embodiments, the sensor further determines a length of the blood clot during treatment to remove the blood clot.

In some embodiments, the system further includes a pH sensor for measuring pH of blood downstream of the clot and an indicator for indicating measured pH. In other embodiments, the system further includes an oxygen sensor for measuring oxygen level of blood downstream of the clot and an indicator for indicating measured oxygen. In some embodiments, the pH sensor measures the pH level of the blood downstream of the blood clot to determine the condition of the vessel to assess one or both of a) treatment of the blood clot in response to the pH level indicated by the indicator; and b) desired blood flow rate after blood clot removal.

In some embodiments, the density sensor is positioned proximal of the distal tip of the elongated member. In some embodiments, the density sensor is embedded in a wall of the elongated member. In other embodiments, the sensor is positioned on an outer surface of the elongated member. In some embodiments, the connector is clamped onto a proximal region of the elongated member.

In some embodiments, the system includes a density reader to display a) an initial density reading prior to commencement of a procedure to remove the blood clot; and b) a second density reading after commencement of the procedure to remove the blood clot for comparison to the initial density reading to determine the extent of removal of the blood clot.

In accordance with another aspect of the present invention, a method for determining a state of blood clot removal from a vessel of a patient is provided comprising the steps of:
a) providing an elongated guidewire;
b) inserting the guidewire through vasculature of the patient and adjacent the blood clot;
c) inserting a device to remove the blood clot;
d) either before or after step (c), measuring a density of the blood clot utilizing ultrasound to obtain a first value wherein signals are sent from within the vessel; and
e) during and/or after commencement of treatment of the blood clot, e.g., commencement of use of the clot removal device, measuring the density of the blood clot utilizing ultrasound to obtain a second value for comparison to the first value to determine the extent of removal of the blood clot from the vessel.

In some embodiments, step (e) occurs after the clinician has ended treatment of the blood clot. In some embodiments, the method further comprises the steps of a) determining a length of the blood clot prior to commencement of the procedure to remove the blood clot and b) determining the length of the blood clot after commencement of the procedure to remove the blood clot, e.g., after commencement of use of the clot removal device, to determine a decrease in length of the blood clot. In preferred embodiments, the steps of measuring the density and determining the length of the blood clot are performed using ultrasonic waves. The method in some embodiments can further include visually displaying the first value and the second value on a display as numerals on the display.

The method can further include the step of repeatedly measuring the density after commencement of treatment, e.g., after commencement of use of the clot removal device, to provide real time assessment of blood clot removal.

In some embodiments, the method further comprises the step of indicating to the user the pH level of the blood to enable the user to determine a pH level of the vessel downstream of the blood clot for an initial determination if blood clot removal is advisable, and if advisable, a) a determination of a clot treatment approach; and b) a determination whether slow reperfusion during and/or after removal of the blood clot is warranted. A sensor can be provided on a distal portion of the flexible member for performing the step of measuring a pH level of the blood.

The method can further include in some embodiments the step of inflating a balloon prior to removal of the blood clot to slow reperfusion if a determination is made that slow perfusion is warranted.

In accordance with another aspect of the present invention, a method for tracking blood clot removal from a vessel of a patient is provided comprising the steps of:
providing a guidewire having an ultrasonic density measuring component;
inserting the guidewire through vasculature of the patient and adjacent the blood clot;
determining an initial density of the blood clot utilizing ultrasound wherein signals are sent from within the vessel;
inserting a device to remove the blood clot;
using the device to remove the blood clot, wherein the step of using the device to remove the blood clot occurs subsequent to the step of the determining the initial density of the blood clot; and
determining a density of the blood clot utilizing ultrasound after removal of at least a portion of the blood clot to obtain a second density to compare to the initial density to determine whether the clot has been sufficiently removed.

In some embodiments the method further comprises providing an indicator for displaying the initial and second densities and a connector connects the guidewire to the indicator.

In accordance with another aspect of the present invention, a system and method for assessing vasculature downstream of the clot is provided. This system can be used independently, or alternatively, can be used together with the system and method for assessing the blood clot via density measurement as either separate systems or a single (combined) system. The system of assessing vasculature downstream of the clot enables selection of the best clot treatment method and/or selection of the desirable rate of return of blood flow after removal of the blood clot.

The system for assessing vasculature can be achieved by a system for determining a pH level of blood in a vessel of a patient. A sensor is positioned at the distal portion of the elongated member, e.g., a catheter or a guidewire, for positioning distal of the blood clot and a connector connects the elongated member to an indicator, the sensor measuring the pH level of blood, preferably in a closed or a substantially closed system downstream of the blood clot, to thereby determine pH of the vessel downstream of the blood clot to determine the condition of the vessel to assess subsequent treatment of the blood clot. The indicator provides an indication of the blood pH measured by the sensor.

In accordance with another aspect, a system for assessing vasculature downstream of the clot can include a system for determining an oxygen level of blood in a vessel of a patient. A sensor is positioned at the distal portion of the elongated member, e.g. a catheter or a guidewire, for positioning distal of the blood clot. A connector connects the elongated member to an indicator, the sensor measuring the oxygen level of blood, preferably in a closed or a substantially closed system downstream of the blood clot, to thereby determine the oxygen level of the vessel downstream of the blood clot to determine the condition of the vessel to assess subsequent treatment of the blood clot. The indicator provides an indication of the oxygen level of the blood measured by the sensor.

In accordance with another aspect, the present invention provides a system and/or method for determining treatment after determining a pH level of blood in a vessel of a patient comprising a flexible elongated member, e.g., a catheter or a guidewire, configured and dimensioned for insertion in the vessel of the patient, the elongated member having a proximal portion and a distal portion and configured for insertion so the distal portion extends distal of a blood clot. A pH sensor is positioned at the distal portion of the elongated member for positioning distal of the blood clot and an indicator communicates with the sensor to indicate to a user a measured pH level. The sensor measures the pH level of the blood downstream of the blood clot to determine the condition of the vessel to assess a) treatment of the blood clot in response to the pH level indicated by the indicator; and b) desired blood flow rate during and/or after blood clot removal.

In some embodiments, if the pH level exceeds a predetermined level, blood flow rate is reduced post blood clot removal.

The system may further include a connector connecting the elongated member to the indicator.

The system can further include a catheter positionable over the flexible member. In some embodiments, the catheter has a mechanical device for mechanically removing the blood clot and a balloon distal of the mechanical device inflatable to reduce blood flow to slow reperfusion if a determination is made that slow perfusion is warranted. In other embodiments, the catheter has a lumen to transport cryogenic fluid distal of the blood clot to reduce blood flow to slow reperfusion if a determination is made that slow perfusion is warranted.

The system can provide an indicator to the user of the pH level of the blood to enable the user to determine a pH level of the vessel downstream of the blood clot for a) selection of a treatment method to remove the blood clot and b) a determination whether slow reperfusion during and/or after removal of the blood clot is warranted.

In accordance with another aspect of the present invention, a system for assessing a condition of an organ is provided by measuring a pH level of blood within vasculature of the organ. The pH sensor can measure the pH level of the blood within the vasculature of the organ to assess the condition of the organ.

BRIEF DESCRIPTION OF THE DRAWINGS

Preferred embodiments of the present disclosure are described herein with reference to the drawings wherein:

FIG. 2A is a close up perspective view of the pH reader of FIG. 1;

FIG. 7 is a close up perspective view of the coupler connecting the pH reader cable to the guidewire;

FIG. 8A is a close up view of the guidewire of FIG. 6 positioned distal of the clot and showing the pH sensor on the outer tip of the guidewire;

FIG. 8B is a cutaway view showing the pH sensor embedded in the wall of the guidewire in accordance with an alternate embodiment;

FIG. 8C is a close up view of an alternate embodiment having a pH sensor spaced from the distal tip;

FIG. 9B is a close up view of the distal portion of the catheter of FIG. 9A showing the density sensor within the clot;

FIG. 10 is a close up view of the density reader of FIG. 9A showing a clot density reading;

FIG. 11A is a side view of an alternate embodiment of the system of the present invention illustrating a guidewire coupled to a density reader and showing the guidewire positioned distal of the blood clot;

FIG. 11B is a close up view of the distal portion of the guidewire of FIG. 11A, with the clot broken away to show the density sensor within the clot;

FIG. 12B is a close up view of the distal end of the catheter and guidewire of FIG. 12A, showing retraction of the catheter to expose the density sensor on the guidewire;

DETAILED DESCRIPTION OF PREFERRED EMBODIMENTS

Figure 1:
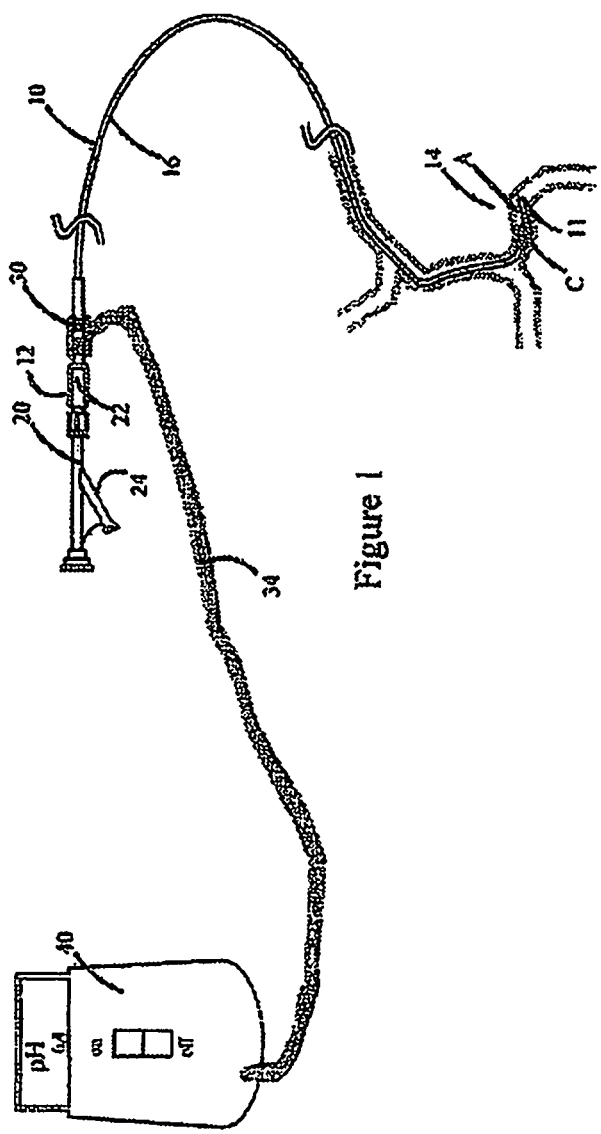
FIG. 1 is a side view of a first embodiment of the system of the present invention illustrating a catheter coupled to a pH reader and showing the catheter tip positioned distal of the blood clot.

The present invention provides a system for determining the type of blood clot. This enables the clinician to assess the best mode of treatment of the blood clot. The present invention further provides a system which can track blood clot removal. The present invention also provides a system for determining the health or condition of the vasculature distal of the blood clot. This aids the clinician in assessing the effect of removal of the blood clot from the vessel. This can also enable the clinician to assess the rate of reperfusion desirable post clot treatment. The foregoing systems can be used independently, or alternatively, two or more of the foregoing systems can be used together. That is, it is contemplated that only one of the systems is utilized so the user measures only one of the parameters, e.g., health of vasculature or type of clot. However, it is also contemplated that two or more of the systems can be utilized so the user can determine the foregoing parameters plus determine, if desired, if the clot has been effectively removed and/or a desired rate of reperfusion. These systems are described in detail below.

Vasculature Determination

Turning first to the system for determining the health or condition of the vasculature, this system is illustrated in FIGS. 1-8, with FIGS. 1-5 illustrating an embodiment where the pH sensor is located on a catheter and FIGS. 6-8B illustrating an embodiment where the pH sensor is located on a guidewire. It is also contemplated that a pH sensor can be positioned on the catheter and on the guidewire, and it is also contemplated that one or more pH sensors can be positioned on the catheter and one or more pH sensors can be positioned on the guidewire. Multiple sensors would enable different regions of the blood (and therefore the vasculature) to be measured. In certain embodiments, utilizing multiple pH sensors, the sensors can be spaced apart sufficiently so that a pH measurement can be taken both upstream and downstream of the blood clot for comparative purposes in assessing vasculature health.

The system for measuring pH is beneficial since in certain instances the vitality of the vasculature distal to the blood clot is compromised once the clot lodges in place. Vasculature that has been deprived of oxygenated blood will necrose and become friable. Once blood flow is restored after clot removal, such blood flow could potentially cause a hemorrhagic event, which means the vessel can bleed out and burst open. Therefore, this system provides a way of determining the health of the vasculature distal to the clot so the physician could determine if clot removal is advisable to determine the best method to remove the clot or take other precautions during clot removal. That is, the physician will be able to determine if the clot should be removed based upon the pH content of the vasculature distal to the clot, and if removal is desirable, assess the best way to restore blood flow as the clot is removed.

Such determination can be done measuring pH of the blood. Thus, the pH level of blood, measured in a simplified cost effective mobile and efficient manner, is utilized to assess the condition of the vessel.

Note the vasculature health can also be accomplished in an alternate embodiment by sensing oxygen levels in the blood which would provide an indication of the health of the vasculature. Other parameters could also be measured.

With respect to pH, it is understood that intracellular pH is important in the maintenance of normal cell function. Blood pH is regulated by a system of buffers that continuously maintain its normal range of 7.35 to 7.45. Blood pH drop below 7 or above 7.45 can cause serious problems, including death. Studies have shown that carbon dioxide plays a vital role in blood pH abnormality. Carbon dioxide serves as a buffer. As carbon dioxide becomes depleted, the pH drops and acidosis and/or apoptosis occurs.

With the presence of a blood clot, there is essentially a closed system (or substantially closed system) created in the vasculature since blood flow downstream of the clot has mostly stopped. Being a closed system, the pH of the blood can be measured and the blood pH will be indicative of the pH of the adjacent vasculature. Thus, the measurement of the blood pH as described herein provides an inexpensive, accurate and effective way to determine the pH and thus the health of the adjacent vasculature. The blood pH can be measured utilizing known techniques such as an ionic potential sensor that converts the activity of a specific ion dissolved in a solution into an electric potential which can be measured. Known glass and crystalline membranes can be utilized.

It is also contemplated that instead of measuring blood pH, the oxygen level of the blood can be measured downstream of the blood clot, preferably in a closed or substantially closed system, to thereby determine the health of the vasculature.

The system of the present invention provides a quick and simple effective measurement of the blood downstream of the clot and enables a determination of blood clot treatment either during or prior to hospitalization, such as in the ambulance ride, wherein the treatment method can be determined so as to prevent cerebral hemorrhaging. This is accomplished without expensive and cumbersome equipment such as MRI machines.

The system in some embodiments not only enables determination of the optimized treatment of the blood clot but in cases where it determines blood clot removal is indicated, it enables control of reperfusion. That is, based on the pH measurement, it provides an indication whether restoration of normal blood flow as a result of clot removal is acceptable, i.e., whether the vessel is in condition to handle restoration of normal blood flow, or whether restoration of blood flow needs to be controlled, i.e., delayed and/or restored slowly until the pH level rises to an acceptable level. Several ways to control reperfusion are discussed below by way of example. Note that the system for measuring pH can be utilized prior to, during and after blood clot treatment to provide indications of pH levels of the blood and thus the vasculature at various times.

Figure 3A:
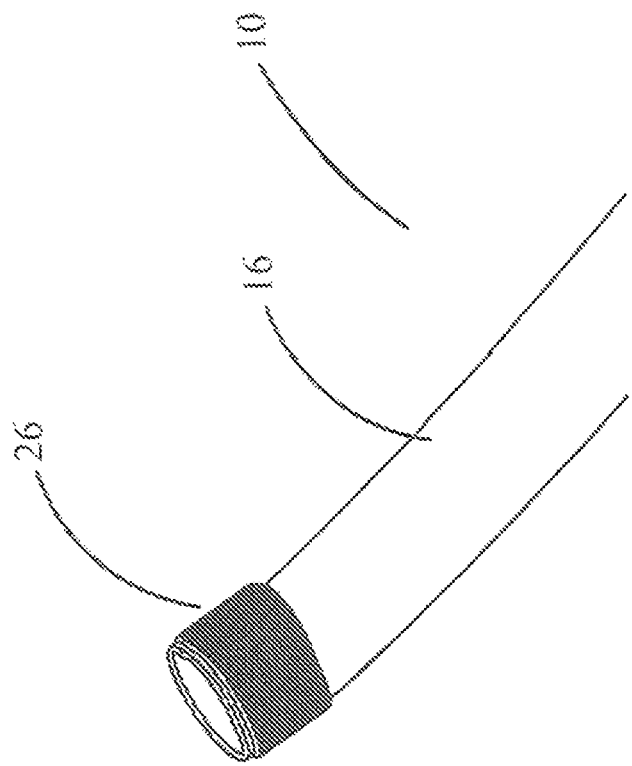
FIG. 3A is a close up view of the catheter tip of FIG. 1 showing the pH sensor on an outer surface of the catheter for determining blood pH.
Figure 3B:
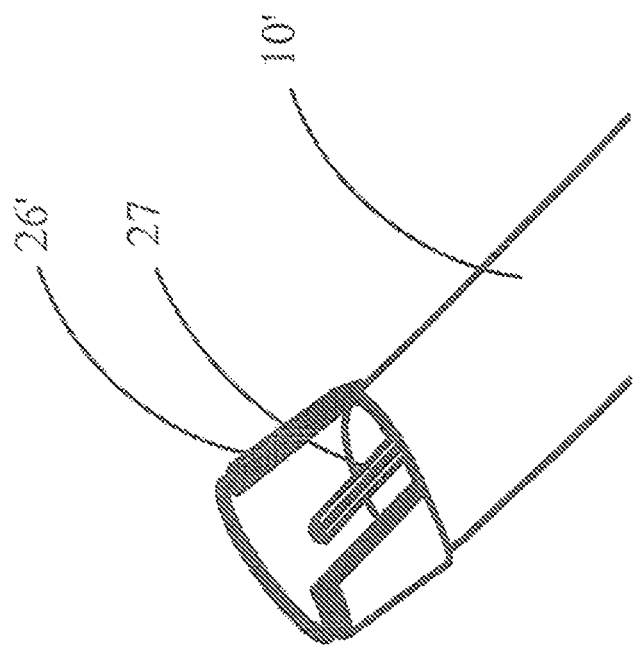
FIG. 3B is a close up view of the catheter tip showing the pH sensor embedded in the wall of the catheter in accordance with an alternate embodiment.
Figure 4:
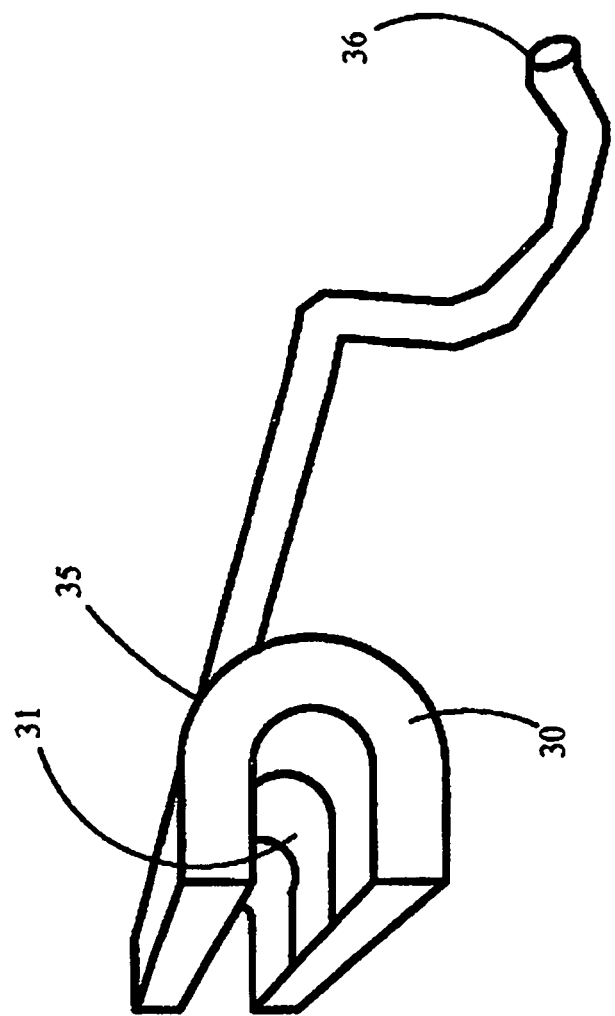
FIG. 4 is a close up perspective of the coupler of FIG. 1 for connecting the pH reader cable to the catheter.
Figure 5:
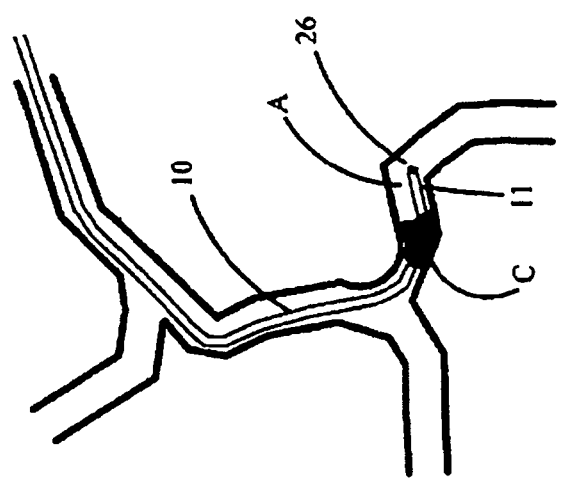
FIG. 5 is a close up view of the vasculature illustrating the catheter tip of FIG. 1 positioned past a blood clot.

Turning more specifically to the system of FIGS. 1-5, catheter 10 has a proximal portion 12 and a distal portion 14. The catheter tube 16 is sufficiently flexible to navigate the small vessels while having some rigidity to enable it to be directed around the curves of the vasculature. An RHV (rotating hemostatic valve) 20 is attached to the catheter hub 22 and includes a side arm 24 for fluid injection and/or aspiration. Coupler (connector) 30 is attached to the catheter 10, and is connected to cable 34 which is connected to pH reader (meter) 40. In one embodiment, as shown in FIG. 4, the coupler 30 is u-shaped with opening 31 between the legs of the "u" dimensioned to frictionally clamp onto the outer wall of the catheter 10. That is, the coupler 30 is shown in the embodiment of FIG. 1 in the form of a U-shaped clip with the radius of the U smaller than that of the outer wall of the catheter so it flexes outwardly when placed over the strain relief of the catheter and then is frictionally retained on the catheter. In another embodiment, a second connector (coupler) half is placed opposite the connector to form a 360 degree clip or clamp surrounding the outer wall of the catheter to retain the connector on the catheter 10. Other methods of attachment are also contemplated such as magnetic attachments. Cable 34 is connected to the coupler at one end 35 and connected at the opposing end 36 to reader 40. As shown (FIG. 1), the coupler 30 is attached to the region of catheter 10 just distal of hub 22, although other locations are also contemplated. The coupler 30 can be attached to the strain relief of the catheter 10 to enhance coupling.

The pH sensor 26 for measuring blood pH is positioned at the distal portion 14 of the catheter 10 and is electrically coupled to cable 34 via a pair of wires (not shown) extending from the sensor 26 to the coupler 30 and/or cable 34. The wires can be embedded in a wall of the catheter 10 or alternatively extend through a lumen in the catheter 10. In the embodiment of FIG. 3A, the sensor 26 is positioned on an outer wall of the catheter 10, extending circumferentially around 360 degrees. The sensor can also be incorporated into a marker band at the tip of the catheter 10. In the alternate embodiment of FIG. 3B, the sensor 26' is positioned inside the catheter 10, either internal of the inner catheter wall or alternatively embedded in the wall of the catheter 10'. Wires 27 connect the sensor 26' to the coupler 30 and/or cable 34, with two lines coming into the reader 40 and extending to the sensor 26.

The pH reader 40 provides an indicator device and contains an on off switch 42. A reading 44 provides a visual indication, as a numeric value, of the measured pH of the blood to inform the user of the pH of the blood, and therefore the vasculature. FIG. 2 shows by way of example a reading of 6.4 which is below the normal range of 7.35 to 7.45 and thus indicates acidosis has likely occurred which affects (compromises) the vasculature structure.

In some embodiments, a pH level of 6.8 is used as the parameter to modify the treatment modality. In other embodiments, the pH level of 6.4 is used as the parameter to modify the treatment modality. By way of example, 6.8 could be a first predetermined level where if the measured pH is at or below this level, the clinician would decide that blood clot removal provides some risk and the method of clot removal needs to be assessed. By way of example, 6.8 could be the threshold for assessing the type of treatment method and a pH level of 6.4 could be the predetermined level where the clot should not be removed because of the condition of the vasculature. In other embodiments, 6.0 could be the predetermined level at which the clot would not be removed.

In some embodiments, a pH level of 6.8 is used as the parameter to modify post treatment reperfusion. In other embodiments, the pH level of 6.4 is used as the parameter to modify post treatment perfusion. By way of example, 6.8 could be a first predetermined level where if the measured pH is at or below this level, the clinician would decide that blood flow restoration post blood clot removal is at risk and blood flow needs to be controlled to gradually restore blood flow. By way of another example, 6.4 can be the threshold for assessing the treatment method if the measured pH is at or below this level, the clinician would decide that blood flow restoration post blood clot removal is at risk and blood flow needs to be controlled to gradually restore blood flow.

Current treatments for clot removal include application of thrombolytic drugs to dissolve the clot, aspiration of the clot and mechanical thrombectomy devices in minimally invasive procedures. A problem encountered with these approaches is that the composition of the clot is undetectable in situ, while the efficacy of these approaches is dependent in part on the clot composition. Therefore, the physician is taking one of the known approaches for treatment of the clot without the knowledge of the clot makeup, e.g., its consistency. This can lead to inconsistent results as well as failure to properly treat the clot.

In use, the catheter 10 (or 10') can be inserted utilizing known methods, e.g., through a femoral approach or a brachial approach, and advanced through the vascular system to the desired treatment site, e.g. a cerebral artery A. The catheter tip 11 is advanced past the blood clot C (see e.g., FIG. 5). The sensor is activated to measure pH, with the pH reader turned on so that pH value can be determined. As noted above, the closed system advantageously enables the user to determine the vasculature condition by measuring the blood pH rather than the pH of the vasculature itself. Proper treatment approaches, e.g., deciding whether the clot can be safely removed, selecting the safest clot removal method or taking other precautions to protect the vessel, can then be implemented. Also, restoration of blood flow can then be controlled in accordance with the condition of the vessel.

FIGS. 6-8B illustrate an alternate embodiment for measuring pH utilizing a sensor on a guidewire instead of the catheter as in FIG. 1. This provides a reduced profile measurement system. It also provides a more flexible system to navigate tortuous vessels. Also, by being smaller it can be inserted more distal within the cerebral vasculature. It could also be more steerable and could traverse the clot easier. In some embodiments, by way of example, the outer diameter of the guidewire can be between about 0.010" and about 0.032", although other ranges of sizes are also contemplated. In some embodiments, the outer diameter can be about 0.014".

Guidewire 50 has a proximal portion 52 and a distal portion 54. The guidewire 50 is sufficiently rigid to navigate the small vessels while having some rigidity to enable it to be directed around the curves of the vasculature. In one embodiment, the guidewire is hollow to form a lumen and the wire(s) runs through the lumen from the sensor to the connector. The wire(s), as in other embodiments herein, is preferably insulated. In another embodiment, the guidewire is a solid core and a polymeric jacket contains the insulated wire(s) on an outer surface of the guidewire. The guidewire 50 is illustrated within a lumen of a catheter 70 having a RHV 74 attached to the proximal end. The RHV 74 is attached to the hub 72 of the catheter 70 and includes a side arm 75 for injection and/or aspiration. Coupler 80 is attached to the guidewire 50, and is connected to cable 83 which is connected to pH reader 40, thus connecting the wire(s) of the sensor to the cable and reader 40. The pH reader can be the same as in the embodiment of FIG. 1. In one embodiment, as shown in FIG. 7, the coupler (connector) 80 is u-shaped with opening 81 between the legs of the "u" dimensioned to frictionally clamp onto the outer wall of the guidewire 50. A two part connector as described above could also be utilized. Other methods of attachment are also contemplated including magnetic attachments for example. Cable 83 is connected to the coupler 80 at one end 85 and connected at the opposing end 86 to reader 40.

The pH sensor 56 is positioned at a distal end of the guidewire 50 and is electrically coupled to coupler 80 and/or cable 83 via a pair of wires (not shown) extending from the sensor 56. The wires can be embedded in a wall of the guidewire 50, or alternatively, the guidewire can have a lumen or channel through which the wires extend. In the embodiment of FIG. 8A, the sensor 56 is positioned on an outer wall of the guidewire 50, extending circumferentially around 360 degrees. The sensor can also be incorporated into a marker band at the tip of the guidewire 50. In an alternate embodiment, the sensor 56' and wires 57 (only one is shown) of guidewire 50' can be positioned inside the guidewire 50', either internal of the inner wall of the guidewire as shown in FIG. 8B, or alternatively embedded in the wall of the guidewire. The catheter 70 through which the guidewire extends can have a marker band 79 for imaging. Note in FIG. 8A, the catheter 70 and guidewire 50 are positioned in a cerebral artery A distal of clot C.

Figure 6:
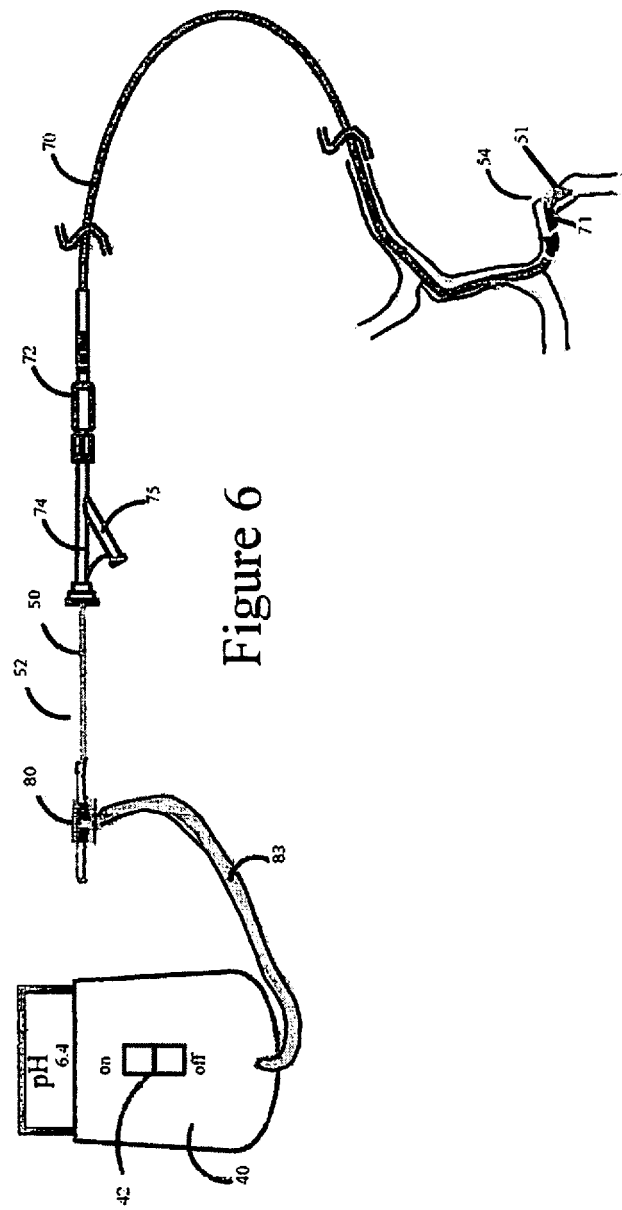
FIG. 6 is a side view of an alternate embodiment of the system of the present invention illustrating a guidewire coupled to a pH reader and showing the guidewire positioned distal of the blood clot.

In use, the switch 42 of the pH reader 40 is activated and the sensor 56 is activated to measure the blood pH and the pH reader provides a numeric pH value of the blood, which is indicative of the pH level of the vasculature. FIG. 6 shows a pH reading of 6.4 by way of example. Note the guidewire 50 can be inserted utilizing known methods, e.g., through a femoral approach or a brachial approach, and advanced through the vascular system to the desired treatment site, e.g. the cerebral artery. In one method, first an introducer is placed in the femoral artery, and a large guidewire and guide catheter is advanced to the carotid artery. The large guidewire is removed, and replaced with a microcatheter 70 and a smaller dimensioned guidewire 50 of the present invention which contains sensor 56. The catheter tip 71 (containing maker band 79 for imaging) of catheter 70 and guidewire tip 51 are advanced past the blood clot C (see e.g., FIG. 8A). The sensor 56 measures the pH and transmits the measurement through the wires extending in guidewire 50 back to the cable 83 which in turn transmits it to the reader 40. As noted above, the closed system advantageously enables the user to determine the vasculature condition by measuring the blood pH rather than the pH of the vasculature (or surrounding tissue) itself. Proper treatment approaches for the treating the blood clot can then be better selected. That is, the physician can determine whether removal of the clot would be too traumatic to the vessel and risk hemorrhaging. The physician can also determine the safe restoration of blood flow and control such blood flow in accordance with the condition of the vessel. Note the different parameters described above are applicable to this embodiment (sensor on the guidewire) as well.

Note the sensors are shown at the distalmost tip of the catheter (FIGS. 1-5) or guidewire (FIGS. 6-8B) but alternatively can be spaced proximal of the distalmost tip such as the sensor 56a of guidewire 50a of FIG. 8C.

The pH sensors can be used in other applications such as in cases of gangrene or tissue dying for some other reason to intravascularly assess the vasculature or health of the tissue.

Figure 2B:
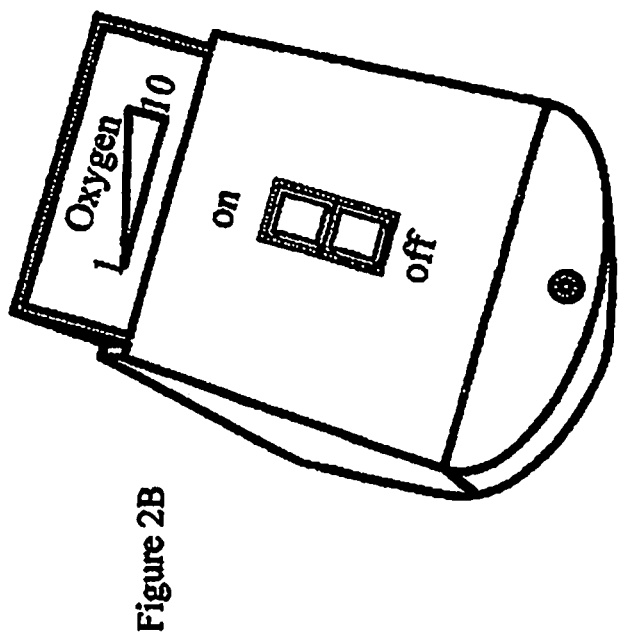
FIG. 2B is a close up perspective view of an oxygen level reader.

In an alternate embodiment, the oxygen level of the blood can be measured which is indicative of the oxygen and thus the health of the vasculature due to the closed or substantially system closed system resulting from the blood clot. The system would be the same as with the above described systems, except one or more oxygen sensors (rather than pH sensors) would be provided on the catheter and/or the guidewire and connected to an oxygen reader (meter) such as shown in FIG. 2B. The oxygen reader provides an indicator of the oxygen level, by providing for example a numeric value, or other indicator, to indicate a range of low to high oxygen level measurements. The sensors can be positioned on the catheter or guidewire in the similar manners of the pH sensors disclosed herein.

FIGS. 14A-14D illustrate one method of use of the present invention illustratively showing the guidewire system of FIG. 6B. In this system, the health of the vasculature is assessed by measurement of the pH level of the blood downstream of the clot so that a) a determination can be made as to how the blood clot can be treated, including whether the blood clot should even be removed; and b) a determination can be made as to how blood flow should be restored.

Figure 14A:
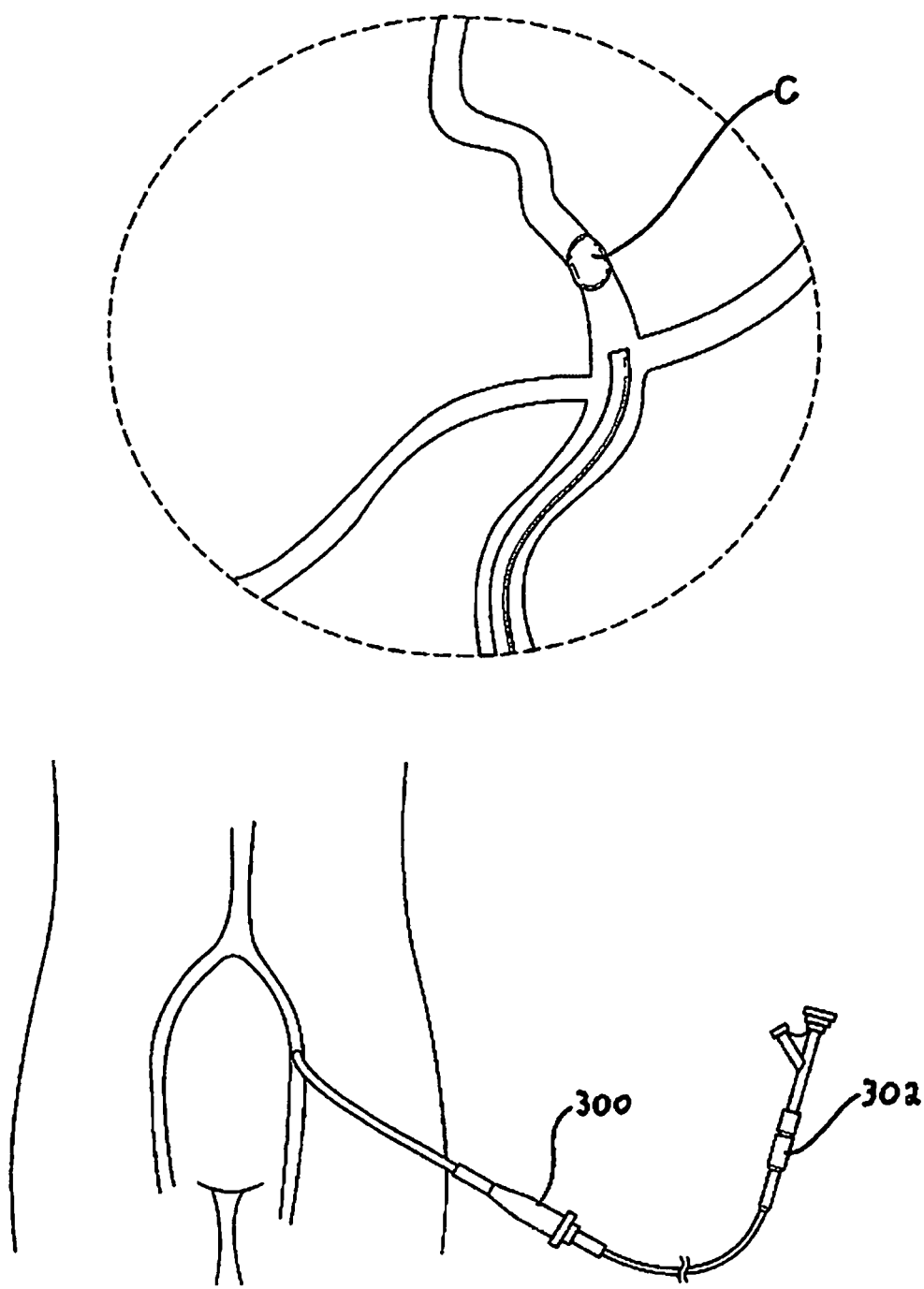
FIG. 14A is a side view illustrating the introducer sheath positioned in the femoral artery and the guide catheter shown advanced into the cerebral artery.
Figure 14B:
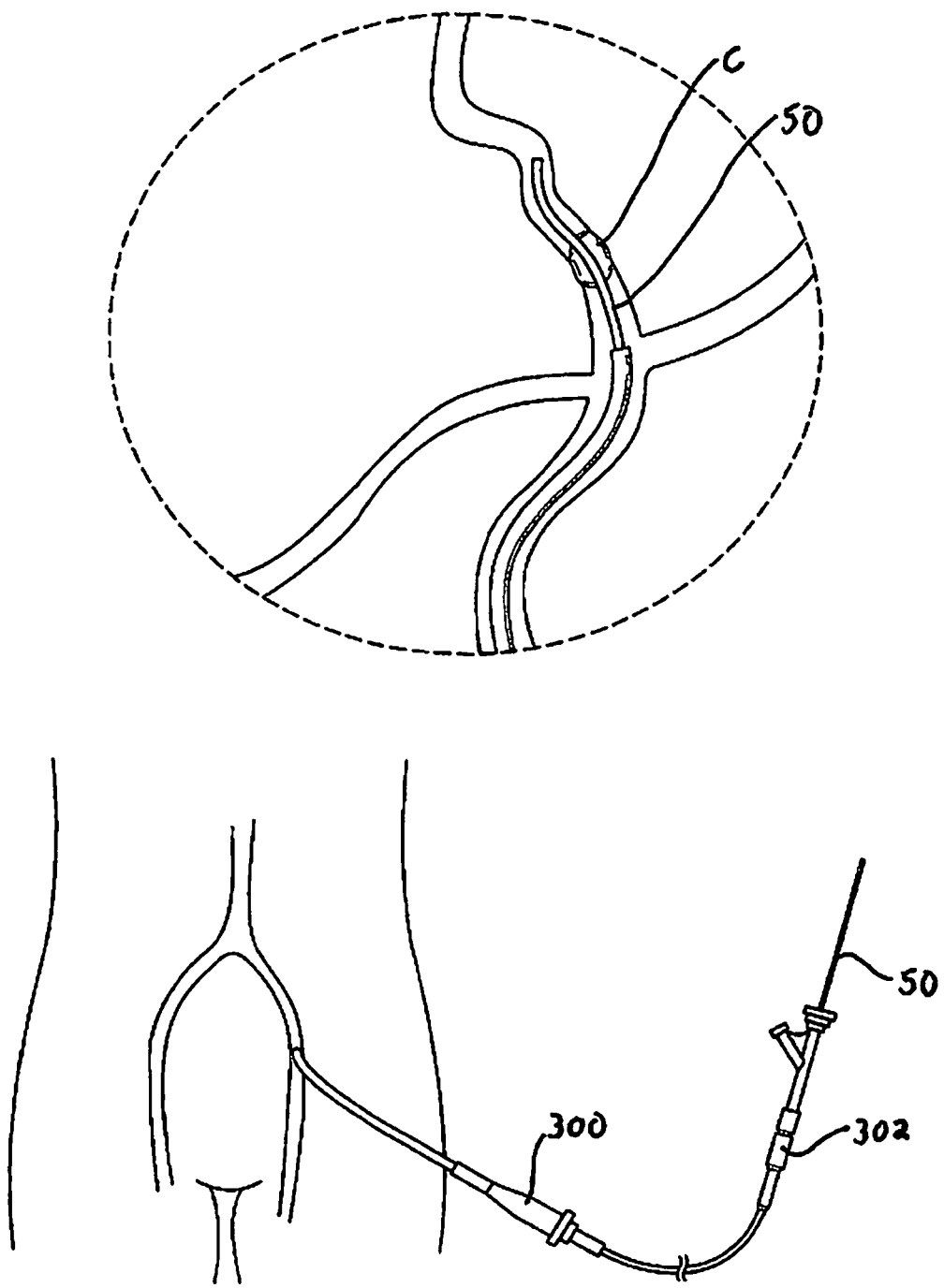
FIG. 14B is a side view similar to FIG. 14A showing the guidewire of the present invention advanced through the guide catheter and past the cerebral blood clot.

FIG. 14A shows a conventional introducer catheter 300 inserted through the femoral artery to provide access to the vascular system. A conventional guide catheter 302 is inserted through the introducer catheter 300 and advanced through the vascular system to or adjacent the targeted cerebral artery, e.g., advanced to the neck region of the patient. The guidewire of the present invention, such as guidewire 50, is inserted through the guide catheter 302 and advanced adjacent the blood clot C as shown in FIG. 14B. (Note the coupler and reader are not shown in FIGS. 14A-14D) The guidewire 50 is then advanced past the clot C to a position downstream of the blood clot (occlusion). The pH level of the blood downstream of the blood clot is measured by the pH sensor as described above (or alternatively by the oxygen sensor if an oxygen sensor is utilized) and the reader provides a readout of the pH level. Based on this reading, the user is made aware of the pH level of the vessel downstream of the clot C, and thus the health of the vessel. This enables the user to determine, e.g., based on comparison to a predetermined pH level, if intravenous thrombolytic therapy, e.g., injection of drugs to break up the clot, aspiration or mechanical thrombectomy to grasp and remove the clot, is the better treatment method, or whether removal of the blood clot is too high risk and therefore should not be removed. The reading also enables the user to determine the effect of blood flow on the vessel downstream of the clot once the blood clot is removed and blood flow is restored.

Figure 14C:
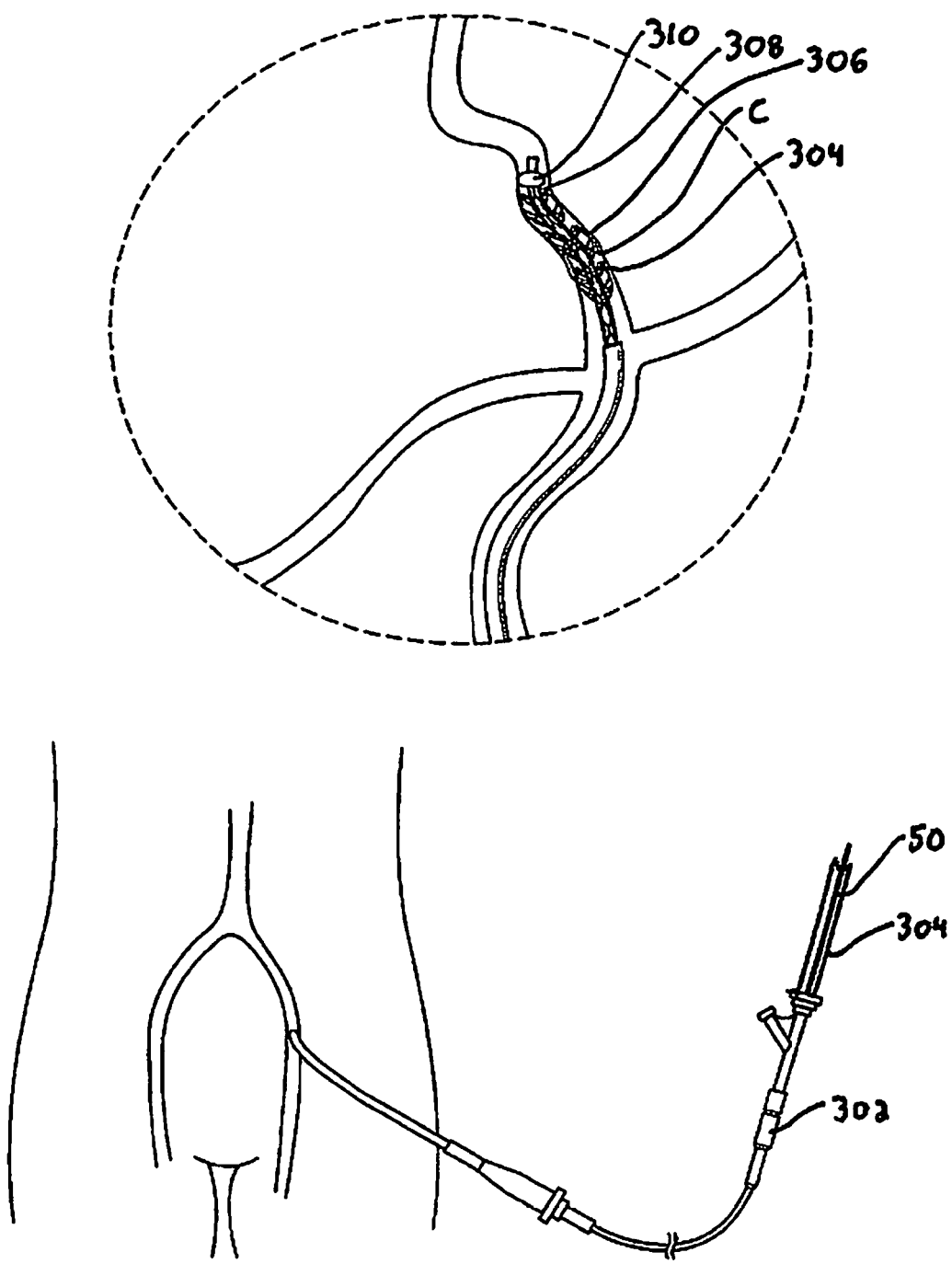
FIG. 14C is a side view similar to FIG. 14B showing a microcatheter for treating the blood clot advanced over the guidewire, and further showing the balloon of the microcatheter inflated to cause slow reperfusion as the blood clot is removed.

FIG. 14C illustrates the next step of inserting a microcatheter 304 over the guidewire 50. The microcatheter selected is based on the health of the vasculature. For example, in FIG. 14C, a mechanical treatment is selected and the microcatheter 304 having a mechanical thrombectomy device 306 such as a stent-like device is inserted over the guidewire 50. Note the mechanical thrombectomy device 306 has an expandable stent structure which when expands captures clot which is removed as the stent is collapsed and withdrawn with the catheter. However, other mechanical thrombectomy devices can be utilized such as motor controlled rotational wires. In the method shown in FIG. 14C, the vasculature has been determined to have a low pH level, for example, below a pH level of 7, or another predetermined level, so the microcatheter selected also includes structure to provide slow reperfusion post clot treatment. More specifically, microcatheter 304 has an inflation lumen 308 and an inflatable balloon 310 positioned at a distal end. The microcatheter 304 is advanced distal of the blood clot C and the balloon 310 is inflated via inflation fluid through lumen 308 prior to, during or after removal of the clot C as shown in FIG. 14C. In this manner, as the device 306 removes the clot C, the blood flow is controlled, i.e., full blood flow is not immediately restored. The balloon 310 can be slowly and partially deflated to gradually restore full blood flow as the pH level rises as determined by the continued measurement of the pH level of the blood by the sensor of the guidewire 50. With the pH level returned to a safe level, the balloon can be deflated and the microcatheter 304 removed with blood flow fully restored. Note the guidewire 50 can be removed from within microcatheter 304 prior to use of the device 306 to remove the blood clot so as not to interfere with the device 306. It can periodically be reinserted within microcatheter 304 to measure the pH level of the blood. In alternate embodiments, the guidewire 50 can be left in place within the microcatheter so the sensor at the distal end can continuously or periodically measure the blood pH. As can be appreciated, in this method, neither a guidewire nor catheter exchange is necessary. In some alternate embodiments, the microcatheter can include the pH sensor so the guidewire could be removed and need not be reinserted for later measurement. As can be appreciated, in this method neither a guidewire nor catheter exchange are necessary.

Figure 14D:
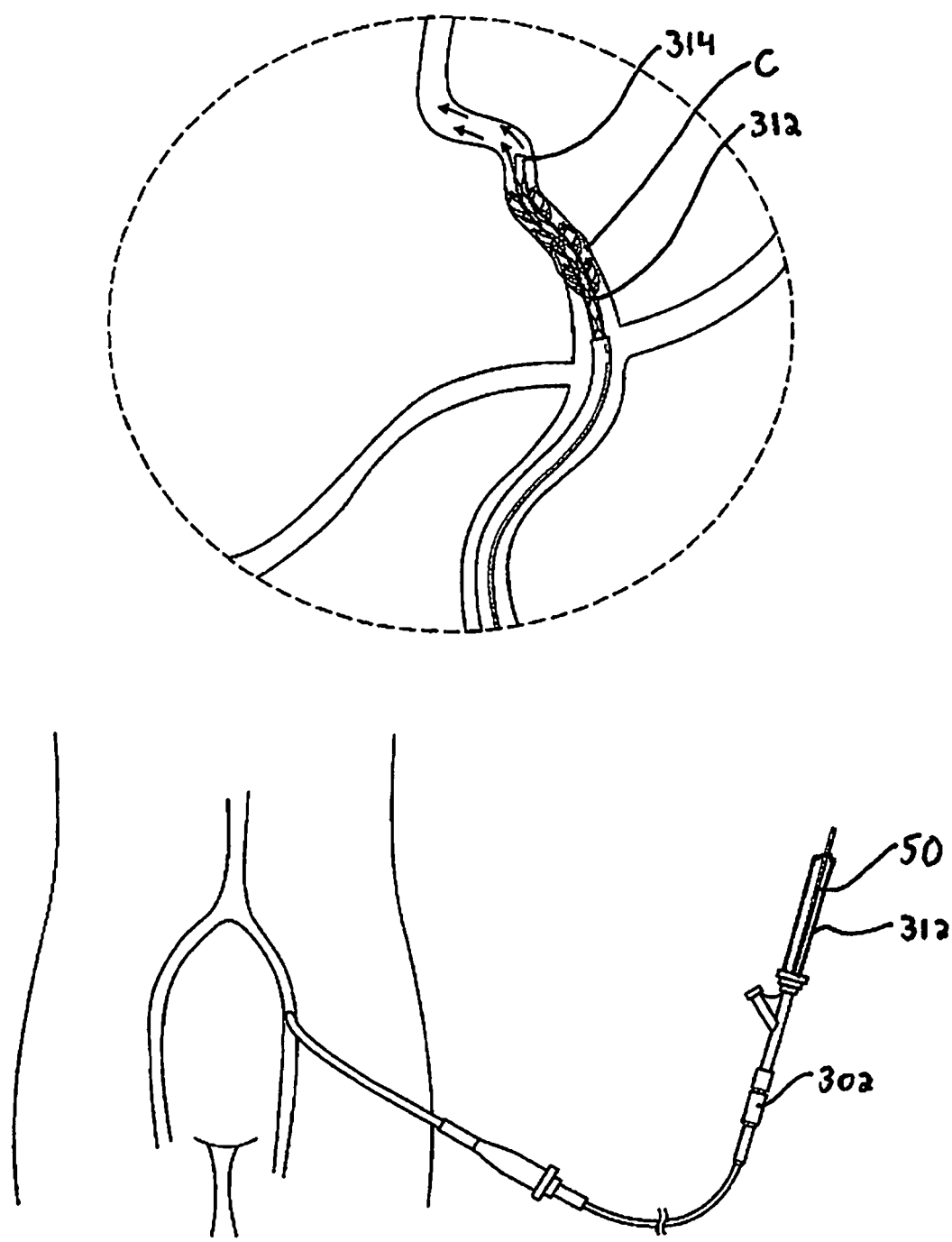
FIG. 14D is a side view similar to FIG. 14C showing an alternate embodiment of a microcatheter for treating the blood clot advanced over the guidewire, and further showing the injection of cryogenic fluid to enable slow reperfusion as the blood clot is removed.
Figure 14E:
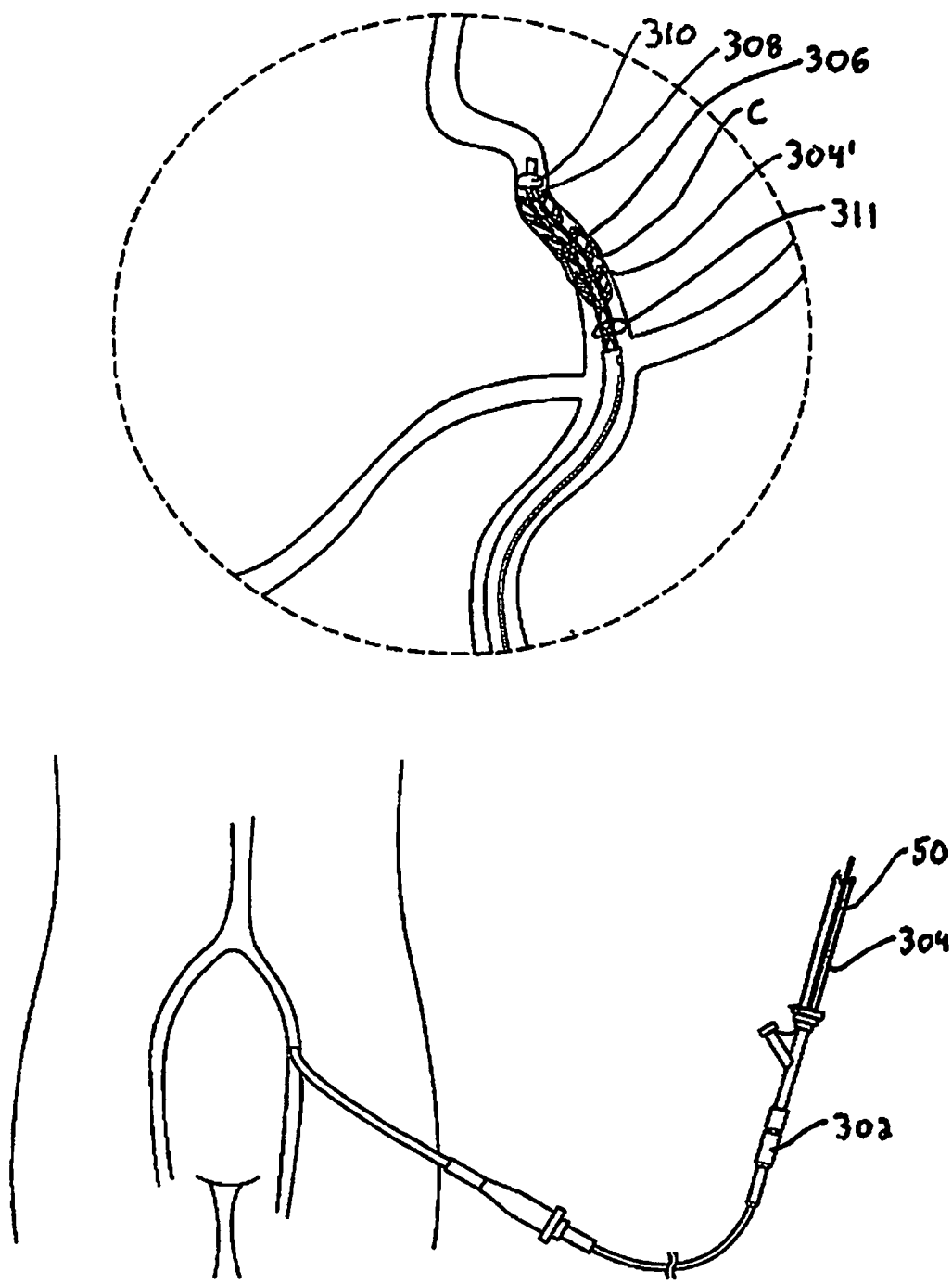
FIG. 14E is a side view similar to FIG. 14C showing an alternate embodiment of a microcatheter for treating the blood clot advanced over the guidewire, and further showing the balloon of the microcatheter inflated as the blood clot is removed.
Figure 14F:
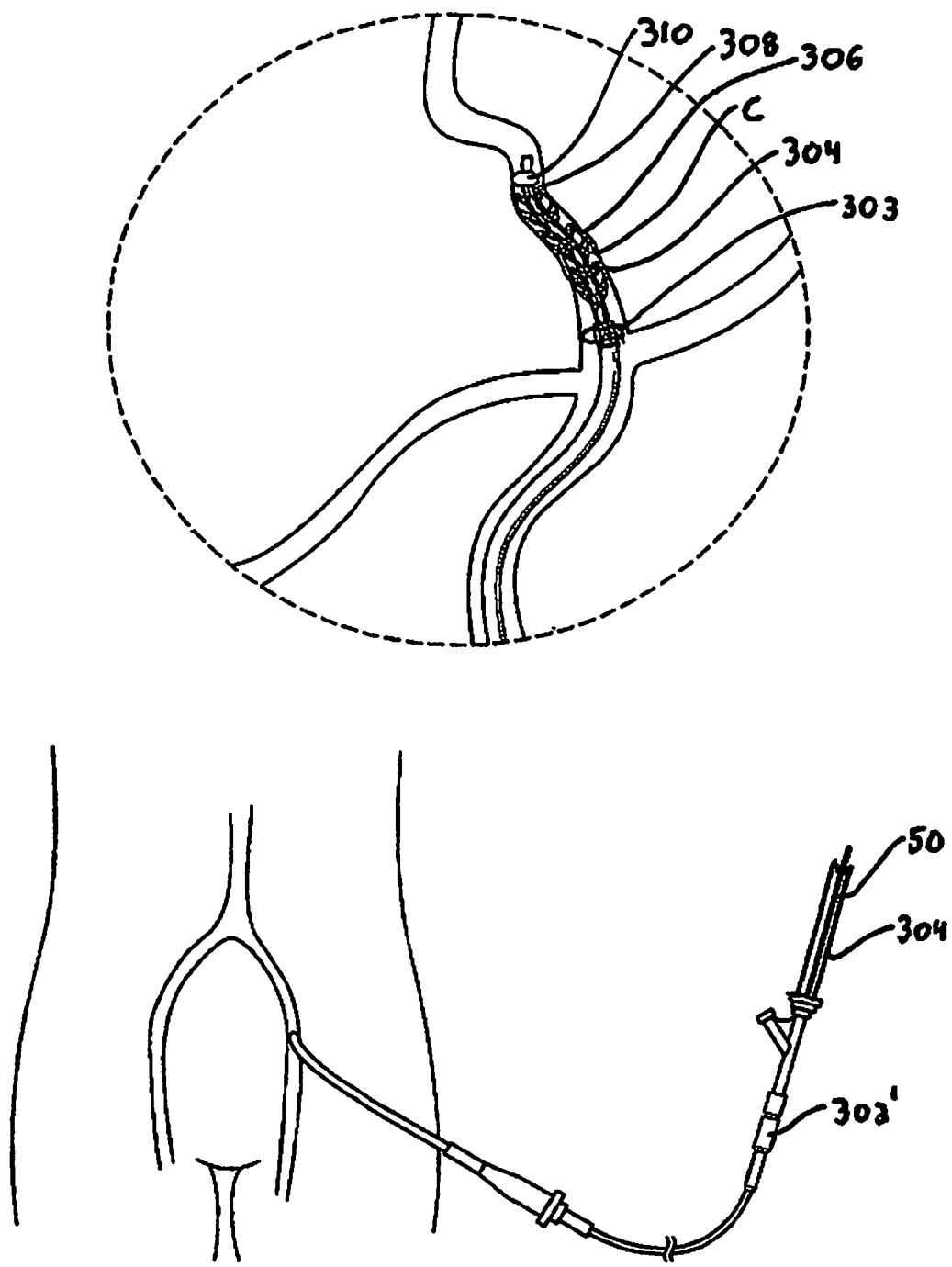
FIG. 14F is a side view similar to FIG. 14E showing an alternate embodiment with a balloon on the guide catheter.

Although the balloon of FIG. 14C is shown distal of the blood clot, it is also contemplated that the balloon can be positioned on the microcatheter proximal of the blood clot as in FIG. 14E. As shown, a balloon 311 can be positioned on microcatheter 304' in addition to or in lieu of balloon 310 to control restoration of blood flow. Alternatively, the guide catheter can have a balloon at a distal end which is inflatable at a position proximal of the blood clot (FIG. 14F). As shown, balloon 303 is positioned on guide catheter 302' and can be provided in addition to or in lieu of balloon 310 (and/or balloon 311). The balloons of these embodiments would block or reduce blood flow until restoration of full blood flow is desired. Thus, such balloons can be expanded proximal and/or distal of the blood clot to control blood flow.

In the alternate embodiment of FIG. 14D, the method of FIGS. 14A-14C is the same except a microcatheter 312 different than microcatheter 306 is utilized when a determination is made, based on a pH level below a predetermined level, e.g., below a pH level of 7, or another predetermined level such as the levels discussed above, that slow reperfusion during or after blood clot treatment (removal) is warranted. Microcatheter 312 has a lumen 314 for injection of cryogenic fluid. Injection of this cooling fluid cools slows the blood flow to provide an alternate method of slowly restoring blood flow post clot removal. The guidewire 50 can be removed from within microcatheter 312 prior to use if desired and periodically reinserted if desired, or alternatively left in place as discussed above. The microcatheter can in an alternate embodiment include a pH sensor.

Note if an interventional therapy treatment is utilized, the catheter to inject the drugs for blood clot removal can have a separate inflation lumen and an inflatable balloon to function to regulate blood flow in the same manner as balloon 310 of microcatheter 304 or can have a lumen, either the same or different from the lumen to inject the drugs, to inject the cooling fluid to slowly restore blood flow in the same manner as microcatheter 312.

Note a comparison is made of the pH level to a predetermined level to determine how to treat the clot. A comparison is also made of the pH level to a predetermined level to determine if slow reperfusion is warranted. These predetermined levels can be the same or different levels. Examples of such predetermined levels are discussed above, as well as other levels, are fully applicable to these embodiments of FIGS. 14A-14F as well.

Further note that the microcatheter can be inserted over the guidewire before or after pH level is measured. Also, in alternate embodiments the guide catheter can be provided with a mechanical thrombectomy device to remove the clot and/or a balloon or cooling fluid lumen so that a separate catheter, e.g. microcatheter 312, need not be utilized.

Also note that microcatheters 304 and 312 are examples of catheters that can be utilized to slow reperfusion, it being understood, that other catheters with other structure to slow reperfusion are contemplated. Additionally, use of the balloon or cooling fluid disclosed herein can be used on catheters other than catheters with the structure of catheters 304 and 312.

In the embodiment of FIG. 1 where a catheter rather than a guidewire is utilized to measure pH levels of blood, a microcatheter with a balloon or lumen for injection of cryogenic fluid can utilized to slowly restore blood flow in the manner described above.

Note the aforedescribed sensors thereby provide a means for measuring the blood pH which can be utilized to determine the health of the vasculature, the reader provides a means for indicating the sensed pH, the microcatheter provides a means for removing the clot and the inflatable balloon or cryogenic fluid provides a means for controlling the rate of blood flow after clot removal.

Note the systems described above assess the blood distal of the blood clot, however, it is also contemplated that assessment of the blood via pH measurement can be performed adjacent the blood clot but proximal to the blood clot in the aforedescribed closed or substantially closed system. Such reading proximal the blood clot can also provide a reading of the vessel vitality adjacent the clot and therefore distal the clot.

Note the aforedescribed systems can alternatively measure oxygen level of the blood rather than pH level as discussed above to determine the health of the vasculature and determine treatment as in FIGS. 14A-14F.

The systems are described herein mainly for use with treating blood clots. However, any of the systems disclosed herein can also be used in other clinical applications. For example, one alternate application is to assess the condition of an organ, e.g., a transplanted organ such as a kidney, by measuring the pH of blood within the vasculature of the organ to assess the condition of the organ. That is, an assessment of pH level in a vessel within the organ to assess vessel vitality will provide an indication of the pH level of the organ to determine the vitality of the organ and whether steps need to be taken to address the organ going bad or potentially not functioning properly.

Clot Determination and Clot Removal Tracking

As noted above, the present disclosure provides a system to identify a parameter such as the composition of a blood clot in a vessel which will enable the physician to scientifically determine the clot makeup and determine the best course of treatment from the available tool sets. This can be achieved in accordance with one embodiment using ultrasound. Such ultrasound system can also be used during the procedure and/or after the procedure to measure clot density so the clinician can determine if the blood clot has effectively been reduced or sufficiently removed from the vessel.

In the embodiment utilizing ultrasonic waves, the density of the clot can be estimated, in vivo, by determining the time it takes for an ultrasonic sound wave to "bounce" back from the clot. The longer the signal takes to return, the less dense the clot is. That is, an ultrasound signal will return more quickly when interacting with a denser substrate. The average densities of traditional "soft" clot and the denser fibrin clot is determined to provide predetermined parameters, and then the system of the present disclosure compares the signal generated by the ultrasonic wave to these parameters to inform the physician of the type of clot. Thus, the system utilizes a logic circuit to determine the makeup of the clot quickly, efficiently and effectively. By way of example, a soft clot can be assigned a numeral 1 and a hard clot assigned a numeral 10, and the clot density measured to assign a value within this range so the physician would first be informed of the type of clot before taking treatment steps, such as removal of the clot. In other words, the measured average densities of both soft clot and fibrin will provide a "baseline" incorporated into the logic-circuit which will determine, in vivo during the surgical procedure, which clot type is present within the vessel. Other numeric values or indicators are also contemplated to indicate varying densities. Thus, the predetermined baseline and the assessment in accordance with this baseline provide a means to provide a density value for the clinician thereby providing a convenient method for the physician to assess the blood clot.

In the system, to generate and provide a digital or analog readout of these ultrasound signals a piezoelectric signal transducer can be used. Piezoelectric materials are crystalline structures which undergo a mechanical deformation when a certain voltage is applied to the crystal. This property is used in conjunction with an applied AC voltage applied to the crystal. As the AC voltage is applied to the piezomaterial it will deform and generate a sound wave. Likewise, when a mechanical load is placed on the piezoelectric crystal a small voltage is generated. This property is used to convert an ultrasonic signal into a measurable voltage. The piezoelectric crystal has a specific voltage/frequency relationship which can be used to convert between the two.

Because of these unique properties, the same piezoelectric transducer which generates an ultrasonic signal can also be used to receive the reflected signal returning from a substrate. Utilizing these properties the ΔT (change in time) can be determined between the sent signal and the received signal by having predetermined the average ΔT for both normal and fibrin clots; the designed logic circuit will be able to determine which clot is present.

This ultrasonic signal is sent from within the vasculature to ensure that interference from cranial tissues, muscle, bone, etc. do not affect measurements. The size and shape of the piezoelectric crystal will determine the distance at which the measurement can be best made.

Figure 9A:
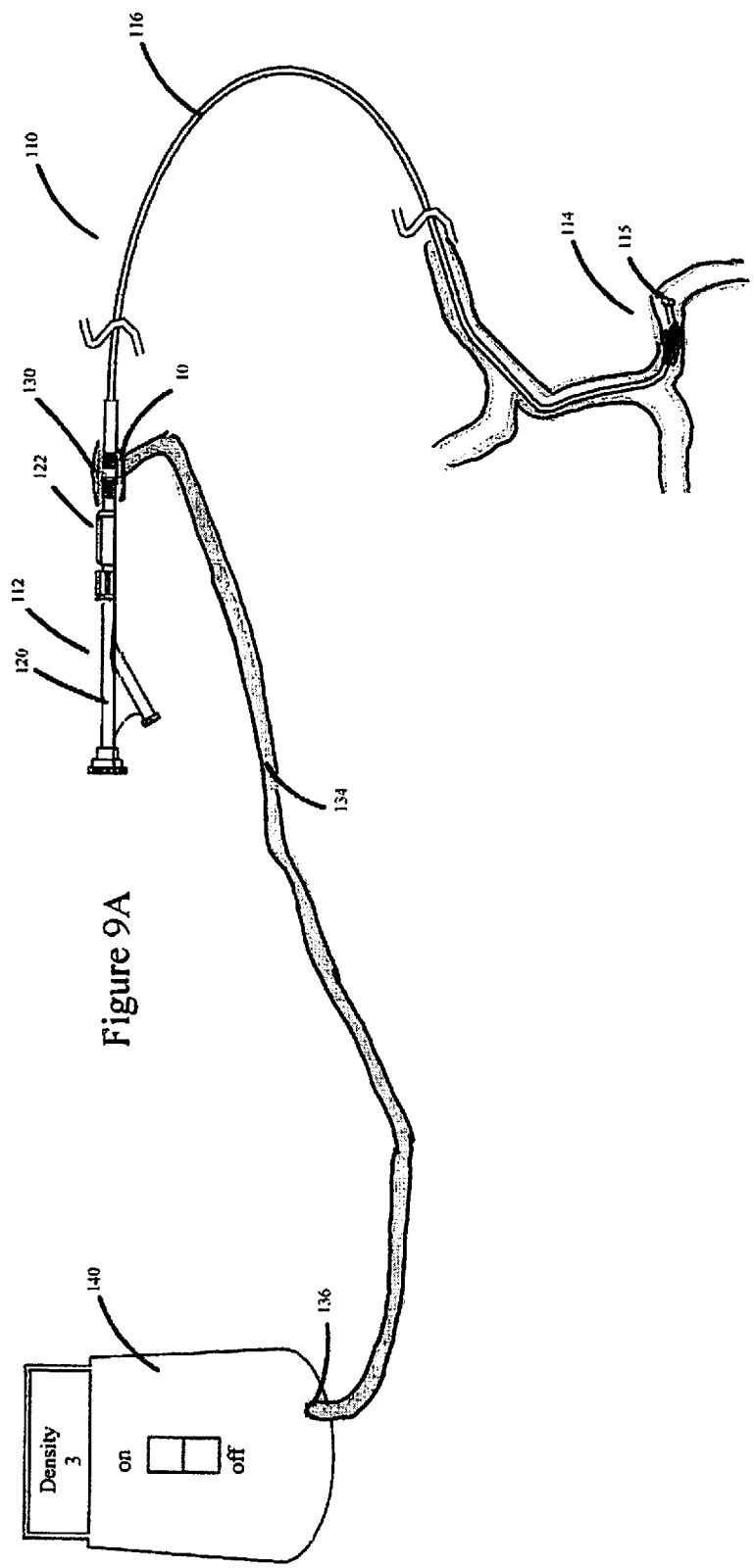
FIG. 9A is side view of an alternate system of the present invention illustrating a catheter coupled to a density reader and showing the catheter tip positioned distal of the blood clot.

Turning now to the system of FIGS. 9A-12B, a system for determining the type of clot is illustrated, with FIG. 9A illustrating an embodiment where the density sensor (utilizing ultrasound as described above) is on a catheter and FIG. 11A illustrating an embodiment where the density sensor (utilizing ultrasound) is on a guidewire. It is also contemplated that a density sensor can be positioned on the catheter and on the guidewire, and it is also contemplated that one or more density sensors can be positioned on the catheter and one or more density sensors can be positioned on the guidewire. This enables more than one region of the clot to be measured which could be beneficial in large clots.

Turning more specifically to the system of FIGS. 9A, 9B and 10, catheter 110 has a proximal portion 112 and a distal portion 114. The catheter tube 116 is sufficiently flexible to navigate the small vessels while having some rigidity to enable it to be directed around the curves of the vasculature. An RHV 120 is attached to the catheter hub 122 and includes a side arm 124 for fluid injection and/or aspiration. Coupler 130 is attached to the catheter 110, and is connected to cable 134 which is connected to density reader (meter) 140. In one embodiment, the coupler 130 can be the same as coupler 30 of the embodiment of FIG. 1 and can be u-shaped with an opening between the legs of the "u" dimensioned to frictionally clamp onto the outer wall of the catheter 110. That is, the coupler can be in the form of a U-shaped clip with the radius of the U smaller than that of the outer wall of the catheter so it flexes outwardly when placed over the strain relief of the catheter and then is frictionally retained on the catheter. In another embodiment, a second connector half is placed opposite the connector to form a 360 degree clip or clamp surrounding the outer wall of the catheter to retain the connector (coupler) on the catheter 110. Other methods of attachment are also contemplated such as magnetic attachments. A cable 134 is connected to the coupler at one end 135 and connected at the opposing end 136 to density reader 140. As shown, the coupler 130 is attached to the region of catheter 110 just distal of hub 122, although other locations are also contemplated.

The density sensor 126 is positioned at the distal portion 114 of the catheter 110, at the distalmost tip 115 and is electrically coupled to cable 134 via a pair of wires (not shown) extending from the sensor 126 to the coupler 130 and/or cable 134. The wires can be embedded in a wall of the catheter 110 or alternatively extend through a lumen in the catheter 110. The sensor 126 in the illustrated embodiment is at the distalmost tip but alternatively could be spaced from the distalmost end so the catheter tip can extend past the clot during use while the sensor is positioned within the clot. The sensor can be positioned on an outer wall of the catheter 110, extending circumferentially around 360 degrees. The sensor can also be positioned inside the catheter 110, either internal of the inner catheter wall or alternatively embedded in the wall of the catheter. The sensor can alternatively be positioned within a marker band on the catheter, with a portion of the marker band removed to expose the sensor. Wires (not shown) connect the sensor to the coupler 130 and/or cable 134.

Figure 15A:
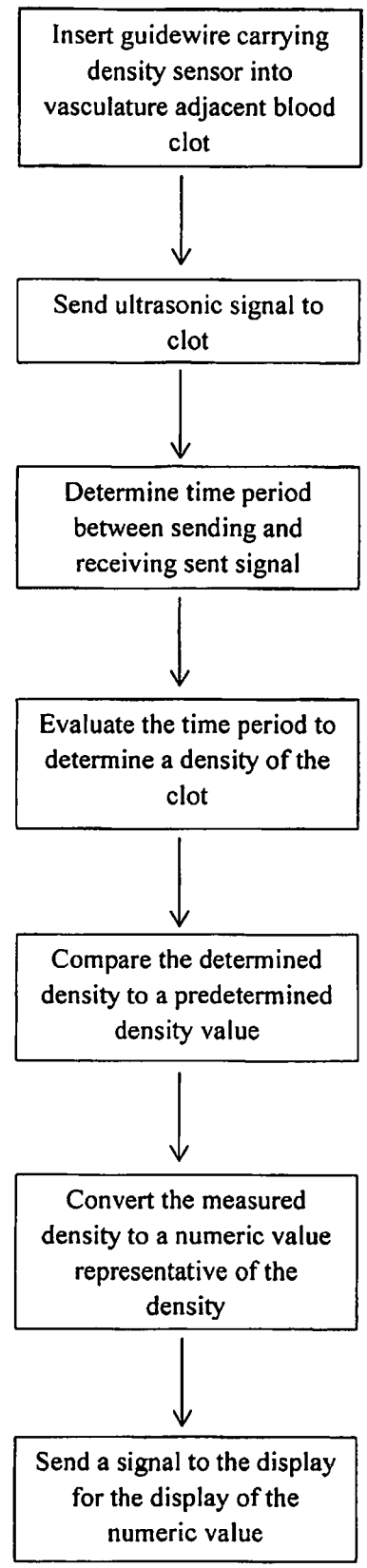
FIG. 15A is a flow chart showing the steps for density measurement and indication in accordance with one embodiment of the present invention.

The density reader 140 provides an indicator device and contains an on off switch 142. A reading 144 provides a visual indication as a numeric value representative of a comparative density as explained above. FIG. 10 shows a density reading of "5" by way of example, indicating a clot density midway between the outer soft clot and outer hard clot range. As noted above, these numerical values are assigned in accordance with predetermined density averages assigned a representative numeric value within a range of values. Connector (coupler 120) is wired to the reader 140 which provides a reading of the clot type based on the signal received from the sensor 126 in response to the ultrasonic signal caused by the ultrasonic waves applied to the clot. Thus, the reader provides a means to display the density, the density displayed in a convenient display as the system processes the time change in sent and received signals to assess density, conducts via an algorithm, a comparative analysis to predetermined density value (e.g., a value of zero), or to predetermined density ranges and then converts it to a numeric value representative of the density within a given range of densities. Thus, the clinician does not need to conduct additional analysis to interpret the measured clot density but can simply rely on the assigned numerical value. This is illustrated in the flow chart of FIG. 15A.

In use, the catheter 110 can be inserted utilizing known methods, e.g., through a femoral approach or a brachial approach, and advanced through the vascular system to the desired treatment site, e.g., the cerebral artery A. The catheter tip 115 is advanced past the blood clot C (see e.g., FIG. 9B) so the sensor 126 is located within the blood clot. The sensor 126 is activated, using ultrasonic waves to measure density, with the density reader providing a visual density indication so the user can decide the optimal way to treat the clot.

FIG. 11A illustrates an alternate embodiment for measuring density utilizing a sensor on a guidewire instead of the catheter as in FIG. 9A. The guidewire provides a reduced profile measurement system. It also provides a more flexible system to navigate tortuous vessels. Also, by being smaller it can be inserted more distal within the cerebral vasculature. It could also be more steerable and could traverse the clot easier. In some embodiments, by way of example, the outer diameter of the guidewire can be between about 0.010" and about 0.032", although other ranges of sizes are also contemplated. In some embodiments, the outer diameter can be about 0.014".

Guidewire 150 has a proximal portion 152 and a distal portion 154. The guidewire 150 is sufficiently rigid to navigate the small vessels while having some rigidity to enable it to be directed around the curves of the vasculature. In one embodiment, the guidewire is hollow to form a lumen and the wires run through the lumen from the sensor to the connector. The wires are preferably insulated. In another embodiment, the guidewire is a solid core and a polymeric jacket contains the insulated wires on an outer surface of the guidewire. The guidewire is illustrated within a lumen of a catheter 170 having a RHV 174 attached to the proximal end. The RHV 174 is attached to the hub 172 of catheter 170 and includes a side arm 175 for injection and/or aspiration. Coupler 180 is attached to the guidewire 150, and is connected to cable 183 which is connected to density reader 140. The density reader 140 can be the same and function in the same manner as in the embodiment of FIG. 10 described above. In one embodiment, the coupler is the same as coupler 80 of FIG. 7 and is u-shaped with an opening in the "u" dimensioned to frictionally clamp onto the wall of the guidewire 150. A two part connector (coupler) as described above can also be utilized. Other methods of attachment are also contemplated such as magnetic attachments. Cable 183 is connected to the coupler 180 at one end 185 and connected at the opposing end 186 to meter (reader) 140.

Density sensor 156 is positioned at a distal end of the guidewire 150, either at the distalmost tip or spaced from the distalmost tip as shown in FIG. 11B, and is electrically coupled to coupler 180 and/or cable 183 via a pair of wires (not shown) extending from the sensor 156 to the coupler/cable. The wires can be embedded in a wall of the guidewire 150 or alternatively the guidewire can have a lumen or channel through which the wires extend. In the embodiment of FIGS. 11A and 11B, the sensor 156 is positioned on an outer wall of the guidewire 150, extending circumferentially around 360 degrees. The sensor can also be incorporated into a marker band at the tip of the guidewire 150. In an alternate embodiment, the sensor can be positioned inside the guidewire 150, either internal of the inner wall of the guidewire in the same manner as in the embodiment of FIG. 8B, or alternatively embedded in the wall of the guidewire. In some embodiments, the guidewire has a marker band with a cut or removed portion to expose the sensor mounted within the marker band. In some embodiments by way of example, the marker band can have an outer diameter of about 0.014" and an inner diameter of about 012". Other dimensions are also contemplated. The catheter 170 through which the guidewire extends can have a marker band for imaging. Note in FIG. 11A, the guidewire 150 is positioned with the sensor in the clot C and the catheter 170 is positioned in a cerebral artery A proximal of clot C.

In use, the density sensor 156 is activated to selectively measure the density of the blood clot and with switch 142 turned on, density indication is provided. The density measurement, comparative analysis, conversion to numeric value, etc. is the same as described above (see also FIG. 15A). Note the guidewire 150 can be inserted utilizing known methods, e.g., through a femoral approach or a brachial approach, and advanced through the vascular system to the desired treatment site, e.g. the cerebral artery. In a preferred method, first an introducer is placed in the femoral artery, and a large guidewire and guide catheter are advanced to the carotid artery. The large guidewire is removed, and replaced with a microcatheter 170 and a smaller dimensioned guidewire 150 of the present invention which contains sensor 156. The catheter tip 171 is advanced past the blood clot C. The guidewire 150 is positioned in the clot and in some embodiments the catheter 170 is withdrawn proximally to expose the sensor 156 within the clot C to measure the density of the clot (in other embodiments, the sensor is exposed so the catheter does not need to be withdrawn). The sensor 156 transmits the measurement through the wires extending in guidewire 150 back to the cable 183 which in turn transmits it to the reader 140. Proper treatment approaches for the treating the blood clot can then be better selected. That is, the reader 140 is used to indicate density measurement so the physician can determine the optimal way to treat the clot. For example, if density measurement determines a soft clot, aspiration can be utilized (mechanical devices are generally not designed for soft clot); if a hard clot, aspiration might not be effective to remove the clot so a mechanical removal device can be utilized. Without density determination, the clinician in certain instances might need to try several different devices to effect satisfactory clot removal which could be more expensive and is time consuming due to withdrawal and insertion of different devices. In short, the pre-treatment density determination provides the clinician with additional knowledge to optimize and increase the efficiency of clot removal.

The system for measuring density to determine approaches to treating the clot, using either the aforedescribed catheter system or guidewire system, can also be utilized additionally or alternatively, to determine the density of the clot after the clot removal procedure has been selected and commenced. Clot removal can be performed for example by a thrombectomy device which has a mechanical component to break up the clot as it is rotated, by an aspiration device which aspirates the clot, or by other methods. During the procedure, as the clot is removed, the density of the clot will decrease. In addition, the length of the clot will decrease as the clot is removed. By taking measurements of the clot during the procedure, an indication can be provided to the clinician (user or physician) of the status of clot removal. Further, either alternatively or in addition, the measurement can be used at the end of the blood clot removal procedure. That is, if the clinician believes the clot has been sufficiently removed, before ending the procedure, the density measuring system can be utilized to determine the clot density and thus confirm the clot has been effectively removed.

More specifically, at the start of the procedure, the density of the clot can be determined by ultrasound waves as described herein to provide an initial value. In one embodiment, this initial value can be the value described above which provides a numerical value for comparison to a predetermined baseline. At any time during the procedure, the user can activate the system to generate the ultrasound waves to measure the density of the clot by measuring the transmitted and received signals as described above. This measurement can be compared to the initial value to ensure the density is decreasing. In certain embodiments, once a certain reduced density level is reached, the clinician is informed that a sufficient portion of the clot has been removed. Such density measuring system avoids the need for the clinician to inject contrast which can in certain instances have the adverse effect of re-compacting the clot.

Figure 16:
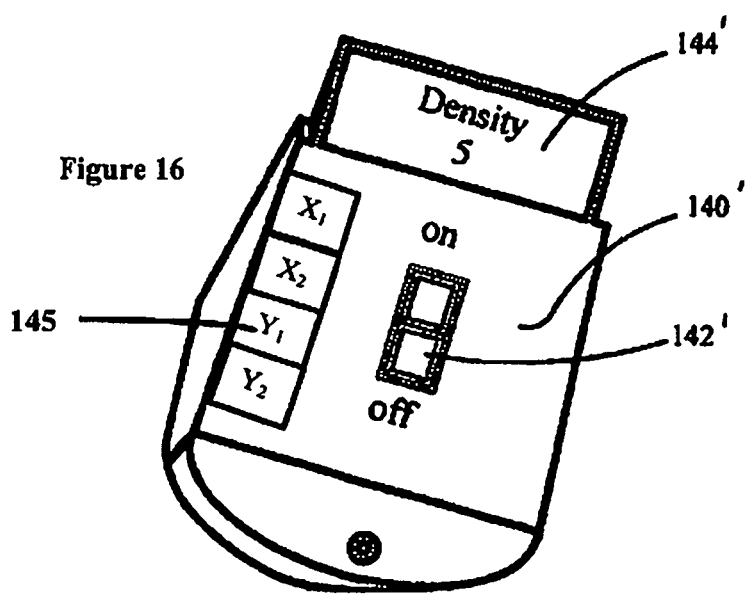
FIG. 16 is a close up view of an alternate embodiment of the density reader of the present invention.

In some embodiments, an initial density value determined at the start of the procedure (represented by "X1" in FIG. 16) can be a value representative of the actual density of the clot. Optionally, another initial value (represented by "Y1" in FIG. 16) can also be representative of the length of the clot. In this embodiment, these two initial values can be recorded and/or indicated on the density reader of FIG. 16, preferably displayed in a window(s) 145 of reader 140' separate from the comparative density numeric value 144', e.g. "5". When during the procedure, the clinician desires to know the clot density and/or length (since a reduction in the length is indicative of the clot being reduced), these measurements can be taken and indicated on reader 140', represented by X2 and Y2, respectively, for comparison to the respective initial values X1, Y1. As the new values (X2 . . . Xn, Y2 . . . Yn) decrease relative to the initial values, the clinician is informed that the clot is being reduced, and after a period of time, indicate that the clot has been effectively removed.

Figure 15B:
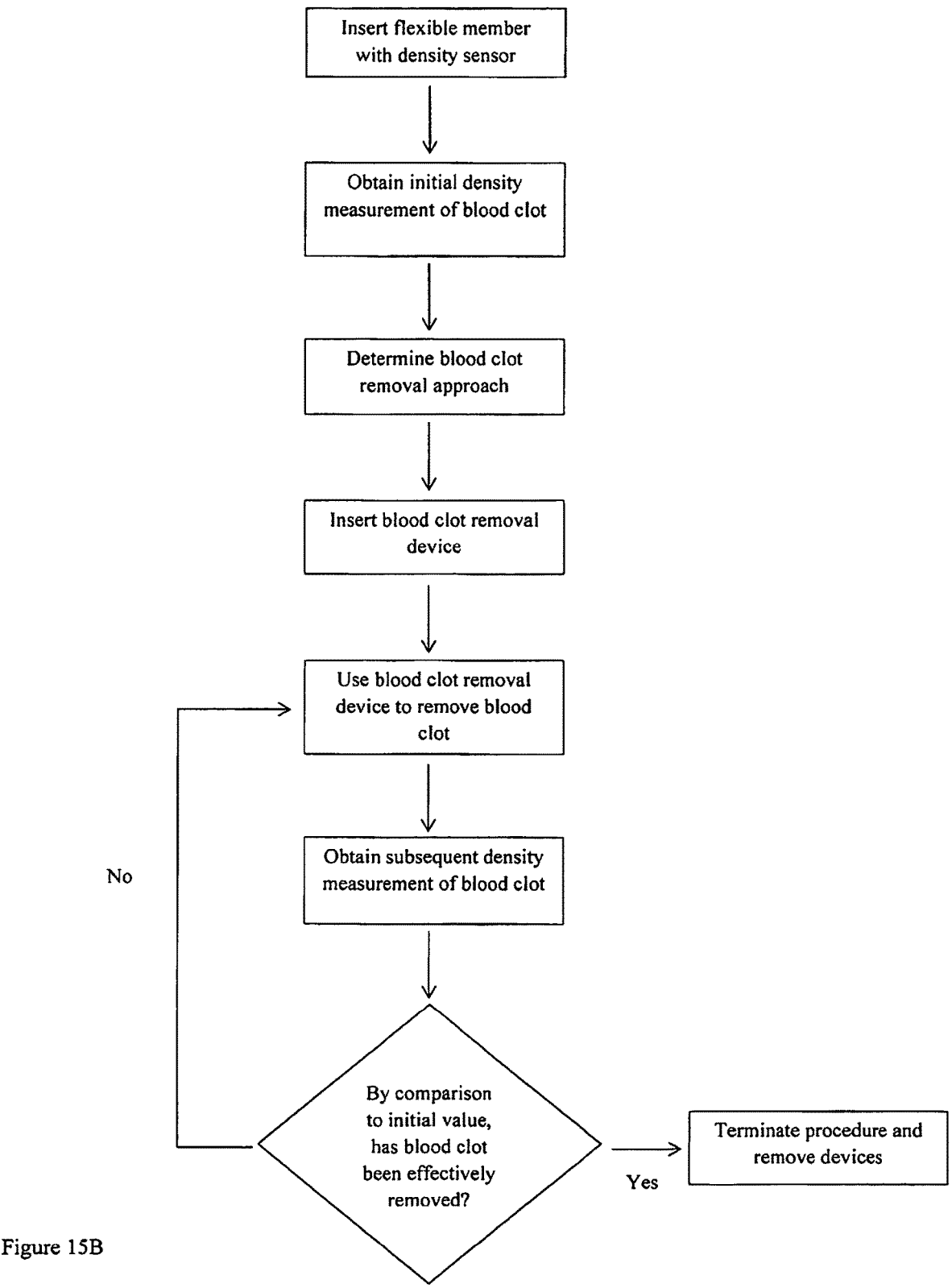
FIG. 15B is a flow chart illustrating the method steps for density tracking of the blood clot in accordance with one embodiment of the present invention.

A method of using the system to determine a state of blood clot removal (i.e., tracking removal) from a vessel of a patient, with reference to the flow chart of FIG. 15, can encompass the steps of inserting an elongated flexible member, e.g., a guidewire or a catheter, having a density measuring component, through vasculature of the patient and adjacent the blood clot, measuring a density of the blood clot to obtain a first value (the first value representative of a density measurement pre-treatment), and to determine a blood clot removal approach, inserting a clot removal device, e.g., a mechanical thrombectomy device or an aspiration device, to remove the blood clot, and after commencement of treatment of the blood clot (by the clot removal device) measuring the density of the blood clot to obtain a second (subsequent) value so that the second value can be compared to the first value to inform the clinician of the extent of removal of the blood clot from the vessel. Obtaining the second value can occur during the treatment or when the clinician believes the clot has been sufficiently removed, e.g., by viewing the collection bag, and therefore believes that treatment can be terminated. Measurements, if desired, can be repeatedly taken during the procedure, i.e., as portions of the clot are removed, to provide real time indication (assessment) of the blood clot removal. As noted above, these values can be displayed on a display to provide a visual indication and/or comparative analysis of the current status of the blood clot. Once the comparison of the subsequent measurement to the initial measurement indicates the blood clot has effectively been removed, the procedure can be terminated and the clot removal device and elongated flexible member with sensor removed from the body.

To further assist the clot treatment determination, the system and method can optionally include the steps of a) determining a length of the blood clot prior to commencement of the procedure to remove the blood clot and b) determining the length of the blood clot after commencement of the procedure to remove the blood clot to determine a decrease in length of the blood clot. Such length determination can be made repeatedly if desired during removal of portions of the blood clot and/or when the clinician believes the clot has been removed.

As noted above, this system and method can be utilized in conjunction with a catheter or guidewire having a sensor for measuring pH level (or oxygen of other parameter) and an indicator to the user of such level of the blood to enable the user to determine a pH level (or oxygen or other parameter) of the vessel downstream of the blood clot utilizing the systems described herein for a) selection of a treatment method to remove the blood clot, including non-removal; and/or b) a determination whether slow reperfusion during and/or after removal of the blood clot is warranted.

Combination of Systems

Figure 12A:
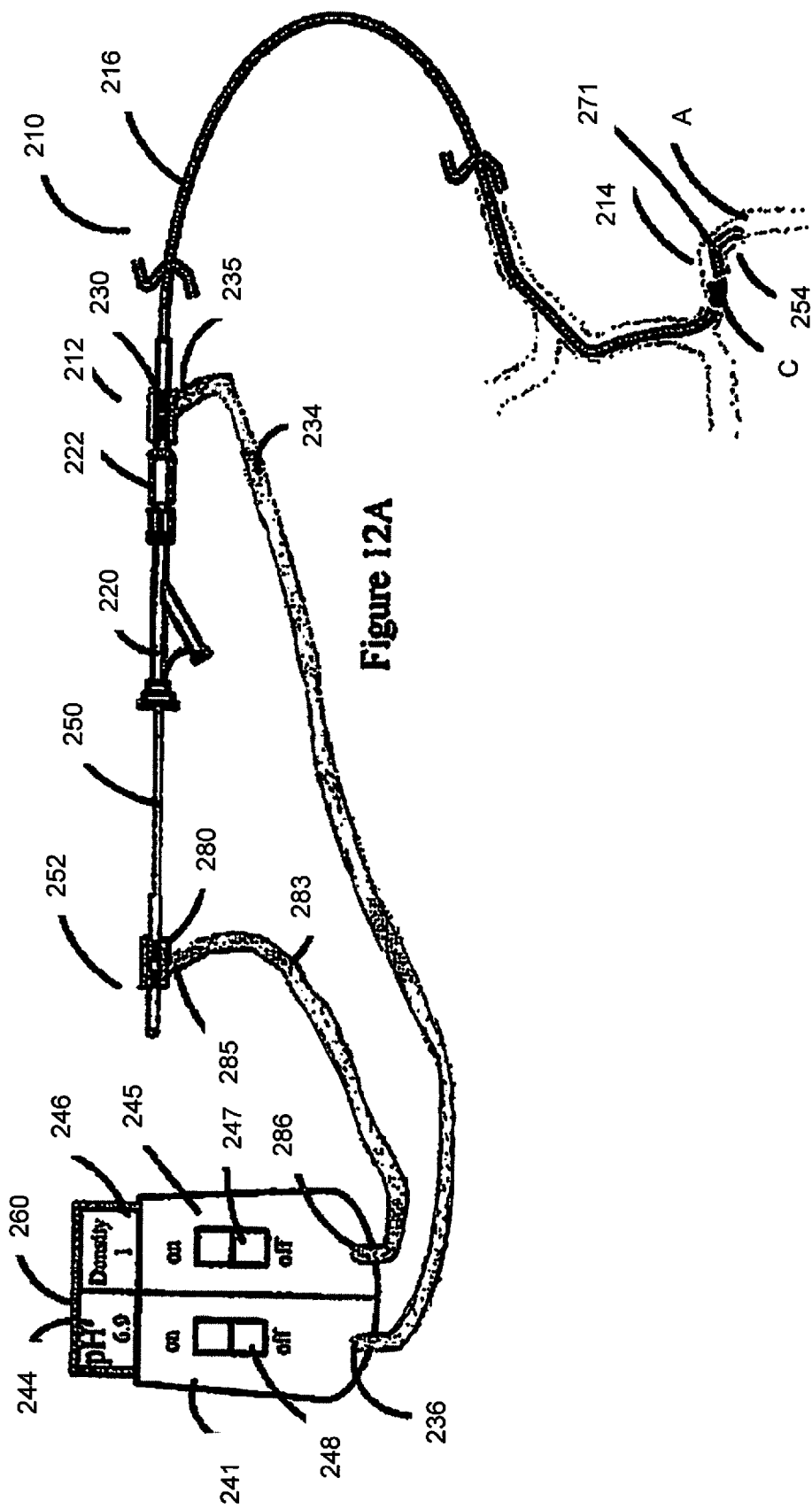
FIG. 12A is a side view of another alternate system of the present invention showing a catheter coupled to a pH reader and a guidewire coupled to a density reader, and further showing the catheter tip and guidewire positioned distal of the blood clot.
Figure 13:
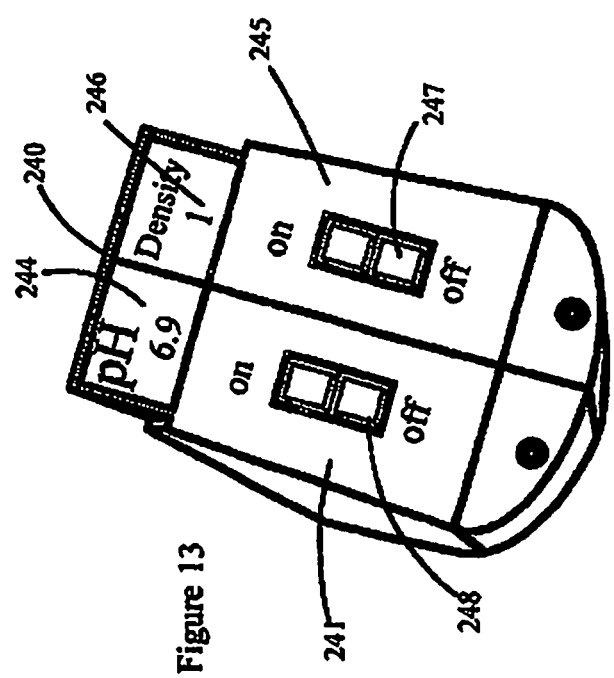
FIG. 13 is an enlarged view of the density and pH reader of FIG. 12A.

It is contemplated that the system for determining clot density (or other clot parameter) and the system for measuring the blood pH (or other blood parameter such as oxygen) can be used together. In such system, both the density sensor and pH sensor (or oxygen sensor) along with a density and pH (or oxygen) reader are provided. Such system is shown in the embodiment of FIGS. 12A-13. The system can also include measuring density to track blood clot removal as described above and the reader described below can be modified to indicate such measurement(s) as in reader 140' of FIG. 16.

Catheter 210 has a proximal portion 212 and a distal portion 214. The catheter tube 216 is sufficiently flexible to navigate the small vessels while having some rigidity to enable it to be directed around the curves of the vasculature. An RHV 220 is attached to the catheter hub 222 and includes a side arm 224 for fluid injection and/or aspiration. Coupler 230 is attached to the catheter 210, and is connected to cable 234 which is connected to pH reader (meter) 241 of reader 240. Reader 240 provides both a pH reading and a density reading. Although shown as a single reader (meter), it is also contemplated that separate meters, such as in FIGS. 2 and 10 could be provided. In one embodiment, the coupler 230 is identical to the embodiment of FIG. 4, being U-shaped with an opening in the "u" dimensioned to frictionally clamp onto the outer wall of the catheter 210. Alternatively, a second connector (coupler) half as described above can be utilized. Other methods of attachment such as magnetic attachment are also contemplated. Cable 234 is connected to the coupler 230 at one end 235 and connected at the opposing end 236 to reader 241. As shown, the coupler 230 is attached to the region of catheter 210 just distal of hub 222, although other locations are also contemplated.

The pH sensor 226, identical to the sensor of FIG. 1, is positioned at the distal portion 214 of the catheter 210 and is electrically coupled to cable 234 via a pair of wires (not shown) extending from the sensor 226 to the coupler 230 and/or cable 234. The wires can be embedded in a wall of the catheter 210 or alternatively extend through a lumen in the catheter 210. In the embodiment of FIG. 12A, the sensor is positioned on an outer wall of the catheter 210, extending circumferentially around 360 degrees in an identical manner as shown in FIG. 3A. The sensor can also be incorporated into a marker band at the tip of the catheter 210. In the alternate embodiment, the sensor can be is positioned inside the catheter 210 (similar to sensor 26' of FIG. 3B), either internal of the inner catheter wall or alternatively embedded in the wall of the catheter. The pH sensor can be positioned at the distalmost tip as shown or alternatively spaced proximally of the distalmost tip. Wires connect the sensor 236 to the coupler 230 and/or cable 224.

The pH reader 241 contains an on off switch 248 to selectively provide a readout of the measured pH. A reading 244 provides a visual indication, as a numeric value, of the measured pH of the blood for the user to determine the pH of the vasculature. A pH of 6.9 is shown by way of example.

Guidewire 250 has a proximal portion 252 and a distal portion 254. The guidewire 250 is sufficiently rigid to navigate the small vessels while having some rigidity to enable it to be directed around the curves of the vasculature. The guidewire 250 is illustrated within a lumen of catheter 210. Coupler 280 is attached to the guidewire 250, and is connected to cable 283 which is connected to density reader 245 of reader 240. In one embodiment, the coupler 280 is the same as coupler 80 of FIG. 7 and is u-shaped with opening in the "u" dimensioned to frictionally clamp onto the wall of the guidewire 250. Alternatively, a second connector (coupler) half as described above can be utilized. Other methods of attachment such as magnetic attachment are also contemplated. Cable 283 is connected to the coupler 280 at one end 285 and connected at the opposing end 286 to reader (meter) 245.

A density sensor 256, which is identical to sensor 156 of FIG. 11B, is positioned at a distal portion of the guidewire 250, spaced proximally of the distalmost tip, and is electrically coupled to coupler 280 and/or cable 283 via a pair of wires (not shown) extending from the sensor. The wires can be embedded in a wall of the guidewire 250 or alternatively the guidewire can have a lumen or channel through which the wires extend. In the embodiment of FIG. 12A, the sensor 256 is positioned on an outer wall of the guidewire 250 in the same manner as sensor 156 of FIG. 11B, extending circumferentially around 360 degrees. The sensor 256 can also be incorporated into a marker band at the tip of the guidewire 250. In an alternate embodiment, the sensor can be positioned inside the guidewire 250, either internal of the inner wall of the guidewire in the same manner as shown in FIG. 8B, or alternatively embedded in the wall of the guidewire. The catheter 210 through which the guidewire 250 extends can have a marker band. Note in FIG. 12A, the catheter 210 and guidewire 250 are positioned in a cerebral artery A distal of clot C. In use, the catheter 210 can be withdrawn with respect to the guidewire 250 to expose the density sensor 256 within the clot as shown in FIG. 12B where the density sensor 256 is proximal of the distal tip (in other embodiments, the sensor is exposed so the catheter does not need to be withdrawn). In the embodiment wherein the density sensor 256 is at the distalmost tip, the guidewire 250 would be withdrawn further proximally until the distalmost tip (and sensor) is positioned in the clot.

In the embodiment where the pH sensor is on the guidewire (as in the embodiment of FIG. 6) and the density sensor is on the catheter (as in the embodiment of FIG. 9A), the catheter need not be withdrawn. The density sensor 256 in some embodiments can be positioned proximal of the pH sensor 226 during use since the density sensor is exposed on the outside of the catheter to measure the blood clot parameter and the pH sensor is exposed on the guidewire to measure the blood parameter downstream of the blood clot. In use, the density sensor is activated to measure clot density and switch 247 of the density reader 245 of reader 240 is turned on to provide a visual numeric indication of a relative density. Density can be measured at various times during the procedure to track clot removal as described above. The pH sensor is activated either simultaneously, or at a different time, so pH reader 241 provides a visual numeric indication of blood pH.

It is also contemplated that in some embodiments a pH sensor (or oxygen sensor) and a density sensor can both be positioned on a single guidewire or a single catheter.

Note the guidewire 250 can be inserted utilizing known methods, e.g., through a femoral approach or a brachial approach, and advanced through the vascular system to the desired treatment site, e.g., the cerebral artery. In one method, first an introducer would be placed in the femoral artery, and a large guidewire and guide catheter would be advanced to the carotid artery. The large guidewire is removed, and replaced with a microcatheter 210 which contains a pH (or oxygen) sensor (or alternatively a density sensor) and a smaller dimensioned guidewire 250 of the present invention which contains sensor 256. The catheter tip 271 is advanced past the blood clot C. The sensor 256 of guidewire 250 is positioned in the clot so the sensor measures the density of the clot and transmits the measurement through the wires extending in guidewire 250 back to the cable 283 which in turn transmits it to the density reader 245 of reader 240. (In the embodiment where the catheter contains the density sensor, the guidewire can contain the pH (or oxygen) sensor. The pH sensor 226 is positioned distal (downstream) of the blood clot to measure pH of the blood distal of the clot and transmit it via wires to the cable and pH reader 241. As noted above, the closed (or substantially closed) system advantageously enables the user to determine the vasculature condition by measuring the blood pH rather than the pH of the vasculature (and surrounding tissue) itself. Proper treatment approaches for treating the blood clot (or not treating the clot as discussed above) and/or restoring blood flow can be better selected. The density reading provides information on the blood clot itself which can be utilized to determine blood clot treatment. The reader can also include readings of density after treatment commences so the user can determine the status of blood clot removal. As noted above, an oxygen sensor can be used in the closed or substantially closed system to determine the vasculature condition.

Note the couplers described herein are preferably coupled to the catheter or guidewire prior to their insertion. However, alternatively, coupling can occur subsequent insertion to facilitate maneuverability to the target site.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed:

1. A method for determining a state of blood clot removal from a vessel of a patient multiple times during a surgical procedure based on density assessment, the method comprising the steps of:
   a) providing an elongated guidewire including a sensor;
   b) inserting the guidewire through vasculature of the patient and adjacent a blood clot;
   c) inserting a device to remove the blood clot, into a region along a length of the blood clot;
   d) either before or after step (c), measuring density of the blood clot with the sensor to obtain a first density value utilizing ultrasound signals and determining a first length of the blood clot with the sensor utilizing ultrasound signals, wherein the ultrasound signals are sent from within the vessel;
   e) after steps c) and d), using the device to remove at least a portion of the blood clot;
   f) after step e measuring the density of the blood clot with the sensor utilizing ultrasound to obtain a second density value for comparison to the first density value to determine the extent of removal of the blood clot from the vessel;
   g) using the sensor to ultrasonically determine a second length of the blood clot after step e) to determine a decrease in a length of the blood clot; and
   h) simultaneously displaying the first density value, the second density value, the first length, and the second length.

2. The method of claim 1, wherein the steps of measuring to obtain the first density value and second density value and determining the first length and second length of the blood clot are performed using measurements of time between transmitted and reflected ultrasonic waves.

3. The method of claim 1, wherein the first density value and the second density value are numerals visually displayed on a display.

4. The method of claim 1, further comprising repeating steps e)-h) to provide real time assessment of blood clot removal.

5. The method of claim 1, further comprising an indicator for simultaneously displaying the first density value representative of an initial density and the second density value and a connector connecting the guidewire to the indicator.

6. The method of claim 1, further comprising the steps of measuring oxygen level of blood downstream of the blood clot and displaying on a display the measured oxygen level.

7. The method of claim 1, further comprising the step of measuring a pH level of the blood, wherein if the pH level is below a predetermined level, reducing the blood flow rate.

8. The method of claim 1, wherein the elongated guidewire includes a marker band and the sensor is positioned within the marker band.

9. The method of claim 1, wherein an indicator numerically displays the first density value representative of an initial density and the first length representative of the blood clot, the indicator further numerically displaying the second density value representative of a subsequent density of the blood clot and the second length representative of subsequent length of the blood clot, for comparison.

10. The method of claim 1, wherein at any time during removal of the blood clot the second density measuring can be activated to generate the ultrasound waves for measuring the second density by measuring the ultrasound signals transmitted and received.

11. The method of claim 1, wherein the step of inserting a device to remove the blood clot comprises inserting a mechanical thrombectomy device.

12. The method of claim 1, wherein the step of inserting a device to remove the blood clot comprises inserting a microcatheter and injecting cryogenic fluid.

13. A method for determining a state of blood clot removal from a vessel of a patient multiple times during a surgical procedure based on density assessment comprising the steps of:
   a) providing an elongated guidewire including a pH sensor and density sensor;
   b) inserting the elongated guidewire through vasculature of the patient and adjacent a blood clot, into a region along a length of the blood clot,
   c) inserting a device to remove the blood clot, into a region along a length of the blood clot;
   d) either before or after step (c), measuring density of the blood clot with the density sensor to obtain a first density value utilizing ultrasound signals, wherein the ultrasound signals are sent from within the vessel;
   e) after steps c) and d), using the device to remove at least a portion of the blood clot;
   f) after step e) measuring the density of the blood clot with the density sensor utilizing ultrasound to obtain a second density value for comparison to the first density value to determine the extent of removal of the blood clot from the vessel;
   g) simultaneously displaying the first density value and the second density value; and
   h) measuring pH level of the blood with the pH sensor and indicating to a user the pH level of the blood to enable the user to determine a pH level of the vessel downstream of the blood clot for:
      (i) a determination of a clot treatment approach to remove the blood clot; and
      (ii) a determination whether slow reperfusion during and/or after removal of the blood clot is warranted.

14. The method of claim 13, further comprising the steps of determining based on the pH level of the blood whether slow reperfusion during removal of the blood clot is warranted and inflating a balloon prior to removal of the blood clot to slow reperfusion if determination is made that slow reperfusion is warranted.

15. The method of claim 13, wherein during removal of the blood clot, a first length and a second length of the blood clot are tracked to detect reduced length.

16. The method of claim 15, wherein an indicator numerically simultaneously displays the first density value representative of initial density and the first length representative of an initial length of the blood clot, the indicator further numerically displaying the second density value representative of a subsequent density of the blood clot and the second length representative of subsequent length of the blood clot comparison.

17. The method of claim 13, further comprising the steps of measuring oxygen level of blood downstream of the blood clot and displaying on a display the measured oxygen level.

18. The method of claim 13, wherein if the pH level is below a predetermined level, reducing the blood flow rate.

19. The method of claim 13, wherein the guidewire includes a marker band and the density sensor for measuring density is positioned within the marker band.

* * * * *